United States Patent
Narayan et al.

(10) Patent No.: US 7,585,675 B2
(45) Date of Patent: Sep. 8, 2009

(54) INHIBITION OF HIV AND SHIV REPLICATION WITH ANTISENSE INTERLEUKIN-4

(75) Inventors: Opendra Narayan, Shawnee, KS (US); Shilpa Buch, Overland Park, KS (US)

(73) Assignee: University of Kansas Medical Center, Kansas City, KS (US)

( * ) Notice: Subject to any disclaimer, the term of this patent is extended or adjusted under 35 U.S.C. 154(b) by 48 days.

(21) Appl. No.: 11/274,387

(22) Filed: Nov. 15, 2005

(65) Prior Publication Data

US 2007/0111958 A1 May 17, 2007

(51) Int. Cl.
C12N 15/00 (2006.01)
C12N 15/88 (2006.01)
C12P 21/06 (2006.01)
C12Q 1/68 (2006.01)
A61K 31/70 (2006.01)

(52) U.S. Cl. ............... 435/455; 435/69.1; 435/458; 435/6; 514/44; 424/93.21; 424/93.6

(58) Field of Classification Search ............ None
See application file for complete search history.

(56) References Cited

U.S. PATENT DOCUMENTS 5,942,253 A * 8/1999 Gombotz et al. ............ 424/501

6,811,780 B2 * 11/2004 Furfine et al. ............ 424/145.1

OTHER PUBLICATIONS

Valentin (PNAS 95:8886-8891, 1988).*
Kedzierska et al (Rev. Med. Virol. 13: 39-56, (2003).*
Barouch et al (Intervirology 2000 43: 282-287).*
Bende et al (AIDS Read. 10(9): 526-528, 530-532 (Sep. 2000).*
Peters (Vaccine 20: 688-705, 2002).*
Potter et al., 2004 (Indian J Med Res, vol. 119, pp. 217-237).*
Titti et al., 2007 (Expert Opin. Emerging Drugs, vol. 12, No. 1, p. 23-48).*
El-Amad et al (AIDS 9(12): 1313-1322, Dec. 1995).*
Schapiro et al (J. Infect. Dis. 177: 477-480, 1998).*
Feinberg et al (Nature Medicine 8(3): 207-210, 2002).*
Sekaly (JEM 205(1): 7*-12, 2008.*
Noble IAVI Report 11(5), 2007, retrieved from http://www.iavireport.org/Issues/Issue11-5/Right.asp on Jun. 3, 2008.*
Article entitled *Inhibition of pathogenic SHIV replication in macaques treated with antisense DNA of interleukin-4*, N.K. Dhillon, et al., Blood, Apr. 2005, vol. 105, No. 8.

* cited by examiner

*Primary Examiner*—Richard Schnizer
(74) *Attorney, Agent, or Firm*—Polsinelli Shughart PC

(57) ABSTRACT

A method of treating or preventing SHIV or HIV infection in a subject comprising administering a therapeutically effective amount of a antisense IL-4. The antisense IL-4 inhibits viral replication in the liver, lungs, spleen, and even the lymph nodes of the subject. Further, the antisense IL-4 can be used in combination with other antiretroviral agents or vaccines.

17 Claims, 14 Drawing Sheets
(5 of 14 Drawing Sheet(s) Filed in Color)

Virus Control     Virus + ASIL-4

CD8

Granzyme B

H&E

Control  ASIL-4 treated

INHIBITION OF HIV AND SHIV REPLICATION WITH ANTISENSE INTERLEUKIN-4

STATEMENT REGARDING FEDERALLY SPONSORED RESEARCH OR DEVELOPMENT

The present invention was sponsored by the National Institute of Health Contracts No. NS40238, A1051220-03, 5P20RR016443, 1R01 MH068212-02 A1, and 1R03 MH062969-02, and the government may have certain rights in the invention.

CROSS-REFERENCE TO RELATED APPLICATIONS

Not Applicable.

BACKGROUND OF THE INVENTION

1. Field of the Invention

The invention relates to a method of preventing or treating human immunodeficiency virus ("HIV") and simian-human immunodeficiency virus ("SHIV") by using antisense ("AS") nucleic acids of interleukin-4 ("IL-4").

2. Description of Related Art

HIV induces a persistent and progressive infection leading, in the vast majority of cases, to the development of the acquired immunodeficiency syndrome ("AIDS"). There are at least two distinct types of HIV: HIV-1 and HIV-2. HIV infection leads to immune incompetence, opportunistic infections, neurological dysfunctions, neoplastic growth, and ultimately death.

HIV uses a receptor-mediated pathway in the infection of host cells. HIV requires contact with two cell-surface receptors to gain entry into cells and initiate infection; CD4 is the primary receptor. CXCR4 ("X4") and CCR5 ("R5"), members of the chemokine receptor family of proteins, serve as secondary co-receptors for HIV isolates that have historically been called tropic for T cell lines or macrophages, respectively. CXCR4 or CCR5, in conjunction with CD4, form a functional cellular receptor for entry of certain strains of HIV into cells.

One analogous model system for HIV infection is the SHIV system. See generally Narayan, U.S. Pat. No. 5,849,994, which is incorporated by reference. The pathogenesis of SHIV in non-human primates is also underpinned by the productive infection of $CD4^+$ T cells and macrophages. In the macaque model, pathogenic X4 SHIV includes $SHIV_{KU-2}$ (Raghavan 1997) and the dual tropic $SHIV_{89.6}P$ (Reinmann 1996, Doranz 1996) are often used to investigate pathenogenesis.

Some studies on the impact of various cytokines in HIV and SHIV have been performed. For example, studies on replication of X4 HIV-1 in human macrophage cultures showed that IL-4 caused significant enhancement of virus replication (Valentin 1998). It was also shown opportunistic pathogens that induce IL-4 could promote replication of the virus in tissue macrophages of SHIV-infected macaques. In that study, *Schistosoma mansoni* eggs, potent inducers of Th-2 cytokines, were injected into the portal vein or intratracheally into SHIV-infected macaques. This resulted in the development of granulomas in the liver and lung in a milieu rich in IL-4. Macrophages comprising the granulomas were shown to be productively infected with the virus. In the same study, it was shown that macrophages in Freund's adjuvant-induced granulomas that were rich in interferon ("IFN")-gamma were poorly permissive for virus replication (Buch 2001). While the use of IL-4 antagonists to treat HIV has been theorized, no anti-viral therapeutic studies have been performed either in vitro or in vivo. See generally Furfine, U.S. Published Patent Application No. 2003/0211104.

The present invention is directed to a novel approach for treating HIV and SHIV viral infection. In the present invention, AS IL-4 was successfully used to inhibit replication of pathogenic SHIV in cultures of macaque $CD4^+$ T cells and macrophages, and importantly, in macaques infected with the SHIV virus. Further, the present invention showed that the peripheral blood of treated animals had larger number of $CD8^+$ T cells and a higher degree of expression of $CD8^+$ than controls. Lymph nodes of treated animals were better preserved and had a prominent increase in numbers of activated $CD8^+$ T cells. The therapeutic use of AS IL-4 therefore suggested that this cytokine does cause enhanced SHIV replication by increasing cellular receptors, and simultaneously by suppressing antiviral $CD8^+$ T cell responses.

BRIEF SUMMARY OF THE INVENTION

In one aspect, is directed to a method of inhibiting SHIV or HIV viral replication in a host cell infected with such a virus, comprising the step of administering to the host cell AS IL-4. The AS IL-4 comprises an antisense nucleic acid molecule that has at least a 50%, 60%, 70%, 80%, 90% and most preferably 100% degree of complementarily to the target sequence. The host cell is preferably a T cell or macrophage, and can be located in various tissues, such as the liver, lung, spleen, and lymph nodes of a subject (e.g., macaque or human).

In yet another aspect, the invention features a method of treating SHIV or HIV infection in a mammal comprising administering the AS IL-4 to the mammal such that the SHIV or HIV infection is treated. In a preferred aspect, the mammal is a human in need of treatment for HIV infection. Administration routes include subcutaneous, intramuscular, intranasal, intraarterial, intravenous, topical, transvaginal, transdermal, or transanal administration. Most preferably, a liposome technique is used for delivery.

In still another aspect, in addition to the AS IL-4, the subject is also administered an anti-viral agent, antibacterial agent, antifungal agent, or anti-protozoal agent to prevent or treat opportunistic infections.

In a further aspect, in addition to the AS IL-4, the subject is also administered a nucleoside analog reverse transcriptase inhibitor, a non-nucleoside reverse transcriptase inhibitors, a protease inhibitor, or a fusion inhibitor.

In still another aspect, in addition to the AS IL-4, the subject is administered a DNA vaccine for preventing HIV.

In another aspect, the invention features treating a subject at risk of SHIV or HIV infection by administering AS IL-4 to the subject.

In another aspect, the invention features pharmaceutical compositions comprising AS IL-4 and a pharmaceutically acceptable carrier.

Additional aspects of the invention, together with the advantages and novel features appurtenant thereto, will be set forth in part in the description, which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

The patent or application tile contains at least one drawing executed in color. Copies of this patent or patent application publication with color drawing(s) will be provided by the Office upon request and payment of the necessary fee.

FIG. 7A indicates viral RNA levels in the lungs, liver and spleen in $SHIV_{89.6}P$-infected macaques indicates viral RNA, in infected macaques given a single dose of AS IL-4, and indicates viral RNA in the animals receiving two injections of the AS IL-4. Viral gag mRNA/million hypoxanthine phosphoribosyl transferse ("HPRT") ratios obtained after real-time RT-PCR are presented. RNA was extracted from three different regions of each tissue and analyzed individually. The first set of medium shaded bars represents the untreated animals, the second set of unshaded bars represents the animals treated once, and the last set of darker bars represents the animals treated twice. FIG. 7B shows p27 staining in the spleen sections of control (upper panel) and treated animals (lower panel).

DETAILED DESCRIPTION OF THE INVENTION

Figure 1:
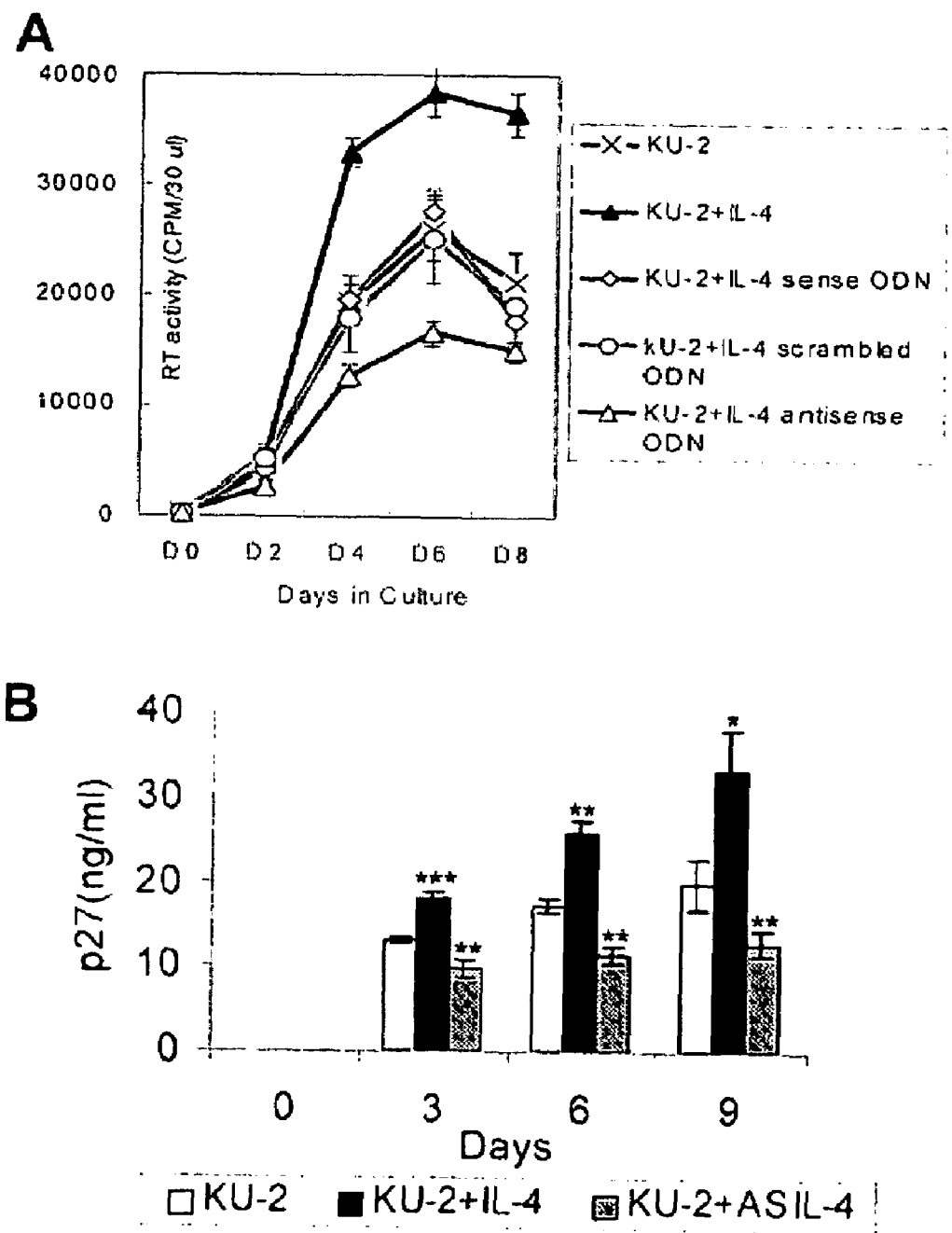
FIG. 1 shows the replication of SHIVKU-2 in response to recombinant macaque IL-4 ("mIL-4") and AS IL-4 in macaque peripheral blood mononuclear cells ("PBMCs") (FIG. 1A) and monocyte derived macrophages (FIG. 1B). The "*" indicates a P value<0.05, and "" a P value<0.005, and a "*", a P value<0.001, compared to control infected cultures.

The present invention is directed to the use of AS IL-4 in the treatment or prevention of HIV or SHIV infection in a subject. The methods of the invention comprise administering a therapeutically effective amount AS IL-4 in a pharmaceutical composition comprising AS IL-4 in a pharmaceutically acceptable carrier to the subject in need.

The term "treating" refers to a process by which the symptoms of a HIV infection are inhibited, delayed, or completely eliminated. Thus, "treating HIV" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating $CD4^+$ T cells), and AIDS (which is defined by more serious AIDS-defining illnesses and/or a decline in the circulating CD4 cell count to below a level that is compatible with effective immune function). Most preferably, the "treatment" is applied to the patient at the outset of infection.

The term "preventing" refers to a process by which an initial HIV infection is prophylactically obstructed or the progression of which is inhibited or delayed. The term "preventing HIV infection" may also encompass treating a person who has not been diagnosed as having HIV infection but is believed to be at risk of infection by HIV.

The term "subject" or "patient" refers an organism at risk of having or actually having HIV, SIV, or SHIV, such as an mammal, including a macaque or human.

The term "therapeutically effective dose" or "therapeutic effective amount" means a dose that produces the desired effect for which it is administered. The exact dose will be ascertainable by one skilled in the art using known techniques.

The term "pharmaceutically acceptable" means approved by a regulatory agency of the Federal or a state government or listed in the U.S. Pharmacopeia or other generally recognized pharmacopeia for use in animals, and more particularly, in humans.

The term "carrier" refers to a diluent, adjuvant, excipient, or vehicle with which the AS IL-4 is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

The term "HIV infection" generally encompasses infection of a host, particularly a human host, by the HIV family of retroviruses including, but not limited to, HIV I (also known as HTLV-III, LAV-1, LAV-2), and HIV II and the like. "HIV" can be used herein to refer to any strains, forms, subtypes, clades and variations in the HIV family. Thus, treating HIV infection will encompass the treatment of a person who is a carrier of any of the HIV family of retroviruses or a person who is diagnosed of active AIDS, as well as the treatment or prophylaxis of the AIDS-related conditions in such persons.

The term "SHIV" generally refers to a number of chimeric viruses constructed by recombinant DNA technology from parental viruses, simian immunodeficiency virus ("SIV") and HIV.

The term "cell" is used in its usual biological sense. The cell can be present in an organism, e.g., mammals such as humans, cows, sheep, apes, monkeys, swine, dogs, and cats. The cell is preferably a mammalian cell, and most preferably a human cell. The cell can be of somatic or germ line origin, totipotent or pluripotent, dividing or non-dividing.

The term "host cell" refers to any cell infected with the virus. The host cell is typically a lymphocyte (such as a CD4$^+$ T lymphocyte) or a macrophage (derived from blood monocytes), or is a precursor to either of these cells, such as a hematopoietic stem cell.

A "vector" is a nucleic acid molecule (typically DNA or RNA) that serves to transfer a passenger nucleic acid sequence (i.e., DNA or RNA) into a host cell. Three common types of vectors include plasmids, phages and viruses. Suitable promoters for expressing the AS IL-4 of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the AS IL-4 in a particular tissue or in a particular intracellular environment.

The AS IL-4 of the present invention may be incorporated into siRNA, which can also be expressed from recombinant viral vectors intracellularly in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. siRNA of the invention can be expressed from a recombinant viral vector either as two separate, complementary RNA molecules, or as a single RNA molecule with two complementary regions. Any viral vector capable of accepting the coding sequences for the siRNA molecule(s) to be expressed can be used, for example vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

As used herein, the terms "complementarity" or "complementary" means that a nucleic acid can form hydrogen bond(s) with another nucleic acid sequence by either traditional Watson-Crick or other non-traditional types of interaction. In reference to the nucleic molecules of the present invention, the binding free energy for a nucleic acid molecule with its complementary sequence is sufficient to allow the relevant function of the nucleic acid to proceed, e.g., AS or RNAi activity. For example, the degree of complementarity between the sense and AS strand of the siRNA construct can be the same or different from the degree of complementarity between the AS strand of the siRNA and the target RNA sequence. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

Based on the foregoing, the AS IL-4 of the present invention thus can contain alterations, substitutions or modifications. For example, the antisense RNA or siRNA can be altered, substituted or modified to contain one or more deoxyribonucleotide bases. Suitable mRNA segments can be identified using the OLIGOENGINE software (Oligo Engine Inc., Seattle, Wash.) to fulfill the requirements for potentially triggering RNAi according to the literature. The nucleic acids can be synthetic or recombinantly produced, including that which differs from naturally-occurring DNA/RNA by the addition, deletion, substitution and/or alteration of one or more nucleotides. Such alterations can include addition of non-nucleotide material, such as to the end(s) of the AS IL-4.

As discussed more fully below, the AS IL-4 can be used as a form of therapy in conjunction with anti-retroviral drugs for treatment of HIV infection. The AS IL-4 can also be used in combination with an HIV immunogenic composition, such as a DNA vaccine. Such immunogenic compositions and vaccines are important to the patient's cellular immunity response in the control of HIV.

One immunogenic composition proposed for combination therapy is set forth in Narayan et al., U.S. patent application Ser. No. 10/941,164 filed on Sep. 15, 2004 entitled "DNA Vaccine Compositions and Methods of Use", which is incorporated by reference in its entirety. In general, this immunogenic composition is directed to a DNA molecule encoding a plurality of viral HIV and SIV proteins in which the virus has been passaged in order to increase the efficiency in which the proteins are expressed. One or more genes are rendered non-functional (e.g., by gene deletion) in order to render the DNA molecule non-pathogenic. In the particular embodiment described therein, the DNA molecule is a SHIV construct comprising a passaged $SHIV_{KU-2}$ virus which is unable to encode functional reverse transcriptase, integrase, and Vif proteins, and further has a 3' long terminal repeat which is at least partially disrupted.

In one aspect, the AS IL-4 of the present invention is incorporated into the DNA molecule of the immunogenic composition itself to form a new vaccine construct. For example, one or more genes of the HIV or SHIV DNA molecule, such as that described in Ser. No. 10/941,164, may be disrupted and substituted with AS IL-4 DNA. The new immunogenic construct may also be administered with a pharmaceutically acceptable carrier and/or adjuvant.

In another aspect, the AS IL-4 of the present invention is administered to the patient with the DNA immunogenic composition, such as the vaccine described in Ser. No. 10/941,164. That is, the AS IL-4 and DNA vaccine are administered as separate nucleic acid constructs.

Standard methods for measuring in vivo HIV infection and progression to AIDS can be used to determine whether a subject is positively responding to treatment with the AS IL-4 of the present invention. Evidence for efficacy of the treatment would include a rise in the count of $CD8^+$ T cell, the cells that are responsible for controlling the infection, stabilization of $CD4^+$ T cells, the cells that are targeted by the virus, and a decrease in viral RNA concentration in the plasma. These are the some suitable indicators that monitor the progress (patient gets worse) or control (patient shows recovery) of HIV in an infected person.

Because of the ethical issues surrounding the treatment or prevention of HIV and AIDS in humans, the present invention uses SHIV infection in macaques as an appropriate model. The present invention is directed to the assessing the extent to which IL-4 modulates SHIV replication in T cells and macrophages. Infection with either $SHIV_{KU-2}$ or $SHIV_{89.6}P$ yielded similar results in cell culture systems.

As discussed more fully below, in the present invention IL-4 activity is inhibited by the use of AS IL-4 nucleic acids. The present invention provides the therapeutic or prophylactic use of nucleic acids comprising at least six nucleotides that are antisense to the genes or cDNAs encoding IL-4 or portions thereof of each. As used herein, IL-4 "antisense" or AS nucleic acids includes nucleic acids capable of hybridizing by virtue of some sequence complementarity to a portion of a RNA (preferably mRNA) encoding IL-4. The term "antisense" or AS includes nucleic acids which are transcribed before hybridizing to the RNA. The antisense nucleic acids may be complementary to a coding and/or noncoding region. Most preferably, the AS nucleic acids of IL-4 are perfectly complementary to the naturally-occurring sense strand.

The antisense nucleic acids of the invention may be double-stranded DNA ("dsDNA") in a plasmid or single-stranded oligonucleotides ("ODNs"). Following administration to cells, the dsDNA is transcribed and messenger antisense IL-4 RNA binds to IL-4 RNA, creating a dsRNA molecule that is destroyed, probably by the same mechanism, that siRNA (see below) causes inactivation. The single-stranded ODNs bind directly to the IL-4 RNA, creating a DNA/RNA hybrid that renders the RNA non-functional. The optimal length of the ODN is about 15 to 50 and most preferably about 25 base pairs in length.

Another type of antisense molecule involves short double-stranded RNAs, known as siRNAs, and short hairpin RNAs, and long dsRNA (>50 bp but usually ≧500 bp). As such, in another embodiment, IL-4 expression is inhibited by a short/short interfering RNA ("siRNA") through RNA interference ("RNAi") or post-transcriptional gene silencing ("PTGS") (see, for example, Ketting et al. (2001) Genes Develop. 15:2654-2659). siRNA molecules can target homologous mRNA molecules for destruction by cleaving the mRNA molecule within the region spanned by the siRNA molecule. Accordingly, siRNAs capable of targeting and cleaving homologous IL-4 mRNA are useful for treating HIV infection and AIDS. The sense and antisense strands of the present siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. The gene-specific inhibition of gene expression by double-stranded ribonucleic acid is generally described in Fire et al., U.S. Pat. No. 6,506,559, which is incorporated by reference. Exemplary use of siRNA technology is further described in McSwiggen, Published U.S. Patent Application No. 2003/01090635; Reich et al., Published U.S. Patent Application No. 20040248174; Chi, Published U.S. Patent Application No. 2005/0026286; and Fosnaugh, Published U.S. Patent Application No. 2003/0148507, which are incorporated by reference.

Methods of Administration

The invention provides methods of treatment comprising administering to a subject an effective amount of AS IL-4. In a preferred aspect, the agent is substantially purified (e.g., substantially free from substances that limit its effect or produce undesired side-effects).

The methods of administration of the AS IL-4 include subcutaneous, intramuscular, intranasal, intrathecal, intraarterial, intravenous, topical, transvaginal, transdermal, or transanal administration. For example, it may be desirable to introduce the pharmaceutical compositions of the invention into the central nervous system by an intraventricular catheter, for example, attached to a reservoir, such as an Ommaya reservoir. Pulmonary administration can also be employed, e.g., by use of an inhaler or nebulizer, and formulation with an aerosolizing agent.

Various delivery systems are known and can be used to administer an agent of the invention, e.g., encapsulation in liposomes, microparticles, microcapsules, recombinant cells capable of expressing the AS IL-4 receptor-mediated endocytosis (see, e.g., Wu and Wu, 1987, J. Biol. Chem. 262:4429-4432), construction of a nucleic acid as part of a viral or other vector, etc.

Administration may be acute or chronic (i.e. daily, weekly, monthly, etc.). Such administration may be alone or in combination with other agents.

Combination Therapies

The AS IL-4 of the present invention can be used therapeutically as the sole method of treatment or in combination with anti-retroviral drugs to reduce the viral load in an HIV infected person and thus prevent AIDS, or prophylactically, in combination with an HIV DNA vaccine, to augment the immunity induced by the vaccine.

Thus, in still other embodiments, the AS IL-4 of the present invention may be administered in combination for example, immunomodulators, antiviral agents, other antiinfective agents or vaccines. For example, the other therapeutic agents used to treat HIV include nucleoside analog reverse transcriptase inhibitors (e.g., zidovudine (AZT), didanosine (ddI), stavudine (D4T), lamivudine (3TC), abacavir, tenofovir, zalcitabine), non-nucleoside reverse transcriptase inhibitors (e.g., delavirdine, nevirapine and efavirenz), protease inhibitors (e.g., ritonavir, saquinivir, indinavir, amprenavir, lopinavir, nelfinavir, atazanavir, entricitabine, fosamprenavir), and fusion inhibitors (e.g., enfuvirtide).

The AS IL-4 may also be used with highly active antiretroviral therapy ("HAART") or in combination with vaccine-based HIV therapeutics. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-lmmunogen, p24 (recombinant), VaxSyn HIV-1 (p24) can be used in combination with a compound of the present invention.

In addition, the other therapeutic agent may be a drug to help treat the opportunistic infections people with HIV infection tend to develop. Antiviral agents to be administered in combination with a compound of the present invention include AL-721, beta interferon, polymannoacetate, HEPT compounds, L,697,639, R82150, U-87201 E and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, rCD4/CD4-IgG, CD4-PE40, butyl-DNJ, hypericin, oxamyristic acid, dextran sulfate and pentosan polysulfate.

Other agents that can be used in combination with the AS IL-4 of this invention are (1) antifungals such as amphotericin B, clotrimazole, flucytosine, fluconazole, itraconazole, ketoconazole and nystatin and the like; (2) antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like; (3) drugs for treating neurological disease such as peptide T, ritalin, lithium, elavil, phenytoin, carbamazipine, mexitetine, heparin and cytosine arabinoside and the like; and (4) anti-protozoals such as albendazole, azithromycin, clarithromycin, clindamycin, corticosteroids, dapsone, DIMP, eflomithine, 566C80, fansidar, furazolidone, L,671, 329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Pharmaceutical Compositions

The present invention also provides pharmaceutical compositions useful for preventing and/or treating HIV, SIV, or SHIV. Such compositions comprise a therapeutically effective amount of the AS IL-4, and a pharmaceutically acceptable carrier and/or adjuvant, such as GM-CSF.

A therapeutically effective dose can be estimated initially from in vitro assays well known to those skilled in the art. For example, a dose can be formulated in animal models to achieve a circulating concentration range that includes the IC50 as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Materials & Methods

1. Viruses $SHIV_{KU-2}$, an X4 virus, was derived by sequential passage of the molecular clone, SHIV-4, which has the env, tat, rev, and vpu genes of HIV-1 HXBc2 (Raghavan 1997). $SHIV_{89.6}P$, a dual tropic X4/R5 virus, was kindly provided by Dr. N. Letvin (Harvard University).

Both viruses were propagated in macaque PBMC cultures. Stock preparations had infectivity titers between about $10^4$ and $10^5$ $TCID_{50}$/ml. Cell cultures were inoculated with either virus at a multiplicity of 0.1.

2. Cell Cultures

PBMCs from macaques were obtained by Ficoll-Hypaque (Sigma, St. Louis, Mo.) gradient centrifugation as described earlier and prepared as suspension cultures grown in RPMI+ 10% FBS+50 U/ml IL2 (R10) (Buch 2001). Briefly, suspensions of PBMC at a concentration of about $1 \times 10^6$ cells/ml of R-10 medium were treated with Staphylococcal enterotoxin A (Sigma) at 5 µg/ml for 24 hours. Cultures were then washed twice with RPMI media and resuspended in R10 and inoculated with SHIV at a multiplicity ("MOI") of 0.01 for four hours at 37° C. The cells were then extensively washed and replenished with fresh R10 and rmIL-4 or AS IL-4 ODN. Every third day, about 0.5 ml of the spent medium was removed from the cultures and replenished with fresh R10 and rmIL-4 or AS IL-4 ODN. Supernatant fluids were collected at regular intervals and monitored for viral p27 by enzyme-linked immunosorbent assay ("ELISA"). Monocyte derived macrophage ("MDM") cultures were obtained from PBMCs by incubation in macrophage differentiation medium consisting of RPMI medium supplemented with 20% heated human serum (56° C. for 30 minutes), 5 U/ml macrophage colony-stimulating factor ("M-CSF"), 100 U/ml granulocyte-macrophage colony-stimulating factor ("GM-CSF"), and 5% heat inactivated rhesus monkey serum at about 37° C. for about 7 days to allow adherent monocytes to differentiate into mature macrophages (Buch 2001). Cells were plated in 96-well tissue culture dishes (Costar, Cambridge, Mass.) or as chamber slide preparations at a concentration of about $8 \times 10^5$ cells/200 µl per well and incubated overnight at about 37° C. Cultures were then rinsed to remove non-adherent cells, re-fed with the same medium, and maintained for 7 days. Macrophages were then inoculated with the virus at an MOI of 0.01 for about four hours at 37° C. Cells were then extensively washed and replenished with fresh medium containing rmIL-4 or AS IL-4 ODN.

3. Interleukin-4

Recombinant macaque IL-4 was provided by Dr. Villinger, Resource for Nonhuman Primate Immune Reagents, Emory University and was used at a concentration of 20 U/ml of tissue culture medium. Cultures were replenished with fresh rmIL-4 every three days.

4. Antisense, Sense and Scrambled Oligodeoxynucleotide ("ODNs")

ODNs used in this study were custom synthesized by Invitrogen Life Technologies (Carlsbad, Calif.). The sequences of the ODNs are as follows:

```
SEQ. ID NO. 1:
Antisense IL-4,     5'GGGCTGCTGCTGGCTTTTTGCTT3'

SEQ. ID NO. 2:
Sense IL-4,         5'AAGCAAAAAGCCAGCAGCAGCCC3'
```

-continued

SEQ. ID NO. 3:
Scrambled IL-4,    5'GGGCTGATGCGGCCTTTTTGCTT3'

The ODNs were used at a concentration of 80 µM in tissue culture medium and replenished every three days. This concentration was not toxic as tested by trypan blue staining (data not shown).

5. Plasmids

Sense and AS IL-4 plasmids were constructed from the rhesus (rh) IL-4 clone provided by the Resource for Nonhuman Primate Immune Reagents. The RhIL-4 plasmid was cut with either BstXI/ApaI (antisense) or with NcoI/NotI (sense) and the restriction fragments obtained were then cloned into the EcoR V restriction site of commercially available pcDNA 3.1 (+) (Invitrogen, Carlsbad, Calif.) by blunt end ligation to generate a CMV-driven RhIL-4 AS, and sense construct, respectively. A green fluorescent protein reporter plasmid gWIZ GFP supplied by Gene Therapy Systems, Inc. (San Diego, Calif.) was also used in the studies. Plasmids were amplified in $E.$ $coli$ (DH10β from Gibco BRL, Carlsbad, Calif.) and extracted by endofree Mega/Giga plasmid purification kit from Qiagen Inc. (Valencia, Calif.). For in vitro experiments, primary macrophages grown in 24-well plates were transfected with 1 µg of plasmid DNA per well complexed with the cationic lipid, in vitro jetPEI-Man (Qbiogene, Irvine, Calif.) as per the manufacturer's instructions.

6. Studies in Macaques

Cynomolgus macaques, approximately three years of age were used in these studies. One animal was used for determination of biodistribution of the gWIZ GFP, and six others for virus and AS DNA studies. The first animal was inoculated IV with 500 µg of the GFP plasmid complexed with the liposome in vivo MegaFectin (Qbiogene Inc., Carlsbad, Calif.) using the enhancer-1, according to the manufacturer's instructions. This animal was killed two days later and lungs, liver, and spleen harvested to assess localization of GFP. The other six animals were inoculated intravenously with 1 ml of stock $SHIV_{89.6}P$. Seven days later, four of the macaques were injected intravenously with the 1 mg of the AS IL-4 DNA complexed with MegaFectin. Two of these animals were given a second injection of the AS IL-4 two days later.

All six animals were killed seven days later for assessment of virus replication in different tissues. The macaques were tranquilized with ketamine and then deeply anesthetized with pentobarbital. Laparotomies were performed and the animals were exsanguinated from the abdominal aorta. A portion of the plasma was collected in ethylene diamine tetraacetic acid ("EDTA") as discussed more fully below.

The animals were perfused via the left ventricle of the heart with 1 liter of saline, and perfusate from the right atrium discarded. Tissues were then harvested rapidly. Portions of each organ were fixed in either 4% paraformaldehyde for histological assays or in Streck fixative (Streck laboratories, Omaha, Nebr.) for immunofluorescence assays. Other portions of the tissues were snap frozen in isomethylbutane chilled with liquid nitrogen. These tissues were used as sources of DNA and RNA.

7. Processing of Blood Samples

Peripheral venous blood collected in EDTA was centrifuged to separate plasma and buffy coats. Plasma was frozen for later determination of plasma viral RNA concentrations. PBMC were separated from buffy coats by centrifugation through Ficoll-Paque density gradients and portions were used for Fluorescence Activated Cell Sorting ("FACS") and ELISPOT assays. A portion of the plasma was collected in EDTA and used for determination of viral RNA content.

8. Virus Assays

Supernatant fluids from virus inoculated cultures were examined for virus content using the reverse transcriptase assay or an ELISA measuring viral Gag p27. Viral RNA concentrations in tissues were assessed using real-time RT-PCR as previously described (Smith 2002). Briefly, total RNA isolated from frozen tissues was treated with DNAase and subjected to real-time RT-PCR (ABI, Foster City, Calif.) over 44 cycles using gag primers and a Taqman Probe (Roche Molecular Systems, Inc.) with thermal cycler conditions as described on ABI PRism 7700. Levels of HPRT mRNA, a housekeeping gene were also measured by real time RT-PCR to normalize the viral load. The amplification efficiencies of the gag and HPRT targets can be considered essentially equal as the difference in their slopes (AS) of the standard curves was within 0.2.

9. FACS Analysis

Leukocytes in whole blood collected in EDTA were analyzed for expression of $CD3^+$, $CD4^+$, and $CD8^+$ T cells surface markers as previously described (Kumar 2001). Briefly, 5 µl of a three-color Ab mix against $CD3^+$ T cell, $CD4^+$ T cell, and $CD8^+$ (BD Biosciences, Rutherford, N.J.) was added to 100 µl of whole blood and incubated for 60 min in the dark. Lysing solution (BD Biosciences) was then added and the samples were incubated for another 20 min at room temperature. Stained cells were fixed with 1% Formalin and analyzed in a BD FACS Calibur flow cytometer. Results were expressed as T cell counts/µl of blood and mean fluorescence intensity ("MFI").

10. ELISPOT Assays

In the present study, Ag-reactive cells was measured using an ELISPOT assay that measured IFN-gamma production by PBMC responding to groups of overlapping 15-mer peptides in the viral Gag, kindly provided by the National Institutes of Health AIDS Research and Reference Reagent Program (McKesson BioServices, Germantown, Md.) as reported earlier (Singh 2005).

11. Immunocyto/Histochemistry

Immunocytochemical analysis was performed on chamber slide preparations of macrophage cultures, on sections from paraffin embedded tissues such as lymph nodes. Slides were treated with murine monoclonal antibody to p27, the Gag protein of SIV (ABI, Columbia, Md.) followed by treatment with biotinylated goat anti-mouse IgG (DAKO, Carpenteria, Calif.), peroxidase-conjugated streptavidin (DAKO), and NovaRed substrate (Vector Laboratories, Burlingame, Calif.), which yields a reddish reaction product (Hicks 2002). For fluorescence microscopy, streck-fixed tissues were frozen, embedded at −25° C. in OCT and cut into 5-10 µm thick sections. Micrographs were captured on a Nikon Eclipse E600 microscope equipped with a 4×/0.13 or 10×/0.30 objective lens, optem 1× DC10 NN camera and analysis image processing acquisition software (Nikon Instruments, Melville, N.Y.). Confocal images were captured on LSM 510 Laser Scanning Microscope with a Plan-Neo 25×/0.80 IK DIC objective lens and LSM software (Carl Zeiss Microscopy, Jena, Germany).

12. Semiquantitative RT-Polymerase Chain Reaction (PCR) Analyses

RNA was extracted from tissue samples using Trizol reagent (Life Technologies, Inc., Grand Island, N.Y.). Semiquantitative RT-PCR analyses were performed on the RNA using the Access RT-PCR kit (Promega, Madison, Wis.) in a Perkin-Elmer (Emeryville, Calif.) DNA Thermal Cycler 480 as described earlier using macaque IL-4 primers (Raghavan 1997) or CXCR4 primers (Wang 1998).

13. Real Time RT-PCR Analysis for IL-4

For quantification of cellular IL-4 mRNA levels, total RNA isolated from macrophages treated with rmIL-4 or AS IL-4 was subjected to real-time RT-PCR using IL-4 primers (SEQ. ID NO. 4: 5'TTT CAC AGG CAC AAG CAG CT3', SEQ. ID NO. 5: 5'GCC AGG CCC CAG AGG TT 3') and Taqman probe (SEQ. ID NO. 6: 5'6FAM-CCG ATT CCT GAA ACG GCT CGA CAG-TAMRA) labeled at 5'end with the reporter dye FAM (6-carboxyfluorescein) and at the 3'end with the quencher dye TAMRA (6-carboxytetramethyl-rhodamine) using ABI Prism7700 (Foster City, Calif.). Primers and the Taqman probe were designed using the Primer Express software (ABI). Thermal cycling conditions consisted of 50° C. for two minutes for uracil-N-glycosylase (UNG), 60° C. for 30 minutes; 95° C. for 10 minutes; followed by 44 cycles of 95° C. for 15 seconds and 60° C. for 30 seconds. Prime RNAse inhibitor was used in the reactions (7.5U, Brinkmann-Eppendorf, Westbury, N.Y.), and reaction volumes were 25 µl. Standard curves were performed using about 6 to 10 fold dilutions of nuclear runoff IL-4 RNA. Samples were analyzed twice, in duplicate. As a measure of cellular mRNA levels, the GAPDH mRNA copy numbers in the RNA samples were also determined by a real-time RT-PCR Taqman assay over 40 cycles (ABI, Foster City, Calif.). The IL-4 mRNA levels were normalized to the cellular GAPDH mRNA number to express the results from an equivalent cell number.

EXAMPLE 1

IL-4 Enhanced X4 Viral Replication of $SHIV_{KU-2}$ in Macague PBMCS, and Macrophages In this example, the effect of IL-4 on the X4 viral replication $SHIV_{KU-2}$ in macque PBMCs, and macrophages in vitro was investigated. The PBMCs were treated with staphylococcal enterotoxin A for 24 hours, after which, the cells were inoculated with the $SHIV_{KU-2}$ virus in the medium containing IL-2 and incubated for four hours at 37° C. Cells were then washed and treated with either rmIL-4 or AS IL-4 ODN which was replenished every third day, as discussed above. FIG. IA shows sequence specific inhibition of $SHIV_{KU-2}$ replication by AS IL-4 ODN in macaque PBMCs.

Macrophage cultures were inoculated with $SHIV_{KU-2}$ and incubated at 37° C. for four hours, after which they were rinsed three times and replenished with medium containing rmIL-4 or AS IL-4 ODN. Every third day, fresh rmIL-4 or AS IL-4 DNA was added to the cultures. Aliquots of the culture supernatant fluid were assayed for SHIV Gag p27 content by ELISA or by reverse transcriptase assays at different time intervals.

As seen in FIG. 1, IL-4 caused significant increases in viral titers of $SHIV_{KU-2}$ in PBMC (FIG. 1A) and macrophage cultures (FIG. 1B), compared to untreated cultures. The experiment illustrated in the drawings is representative of a set of three different experiments. Two tailed t tests were performed. The "*" indicates a P value<0.05, "", a P value<0.005, and"*", a P value<0.001 as compared to control infected cultures.

Figure 2:
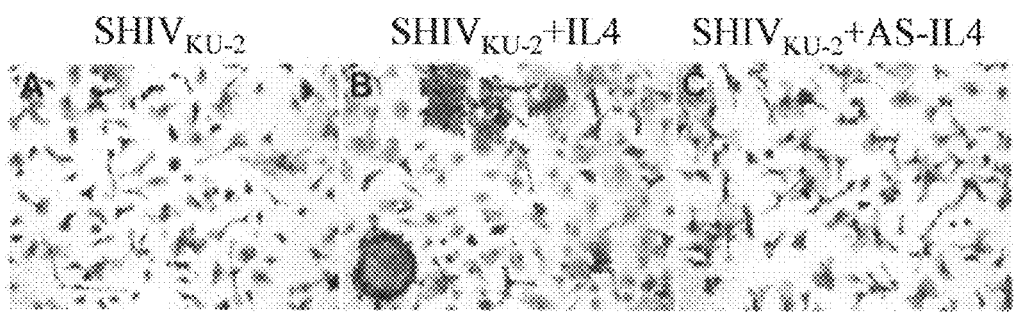
FIG. 2 shows the viral protein staining in $SHIV_{KU-2}$—infected rhesus monocyte derived macrophages ("MDMs") after treatment with IL-4 protein and AS IL-4 ODN.

Furthermore, IL-4 also mediated enhancement of viral replication in a macaque $CD4^+$ T cell line immortalized by Herpes virus Saimiri (data not shown). This enhanced viral replication was also demonstrated by immunocytochemical analyses, showing that IL-4 increased the numbers of virus-positive macrophages, and enhanced viral cytopathic effects characterized by multinucleated giant cell formation (FIG. 2).

The MDM cultures were grown on chamber slides, inoculated with $SHIV_{KU-2}$ for four hours at 37° C., washed, and then treated with either rm IL-4 or AS IL-4 for 48 hrs. Cells were then fixed and immunostained using anti Gag p27 antibody.

EXAMPLE 2

Specific Inhibition of SHIV Replication by AS IL-4 ODNs

In this example, the effect of AS IL-4 ODN treatment on virus replication in macaque PBMC and macrophage cultures was investigated. The cultures were inoculated at an MOI of 0.1, and four hours later treated with either AS IL-4 or various control ODNs. In this experiment, antisense IL-4 DNA was added to virus-inoculated cultures and supernatant fluids collected on days 3, 6, 9, post-infection were assayed for SIV Gag. The cultures were replenished with fresh AS IL-4 ODN every third day. As seen in FIGS. 1A & B, AS IL-4 DNA specifically and markedly inhibited virus replication (80-90%) as measured by reverse transcriptase assays or ELISA. In contrast to cultures treated with IL-4, AS IL-4 ODN decreased the numbers of virus-positive macrophages and the extent of viral cytopathogenicity characterized by multinucleated giant cell formation (FIG. 2). This effect was again confirmed also in the $CD4^+$ T cell line (data not shown). The effect of AS IL-4 ODN on virus replication was sequence-specific since sense and scrambled IL-4 oligos used at similar concentrations did not inhibit virus replication (FIG. 1A).

To further rule out nonspecific effects of IL-4, an irrelevant cytokine, IL-8, served as a control. AS IL-8 ODNs when used at the same concentration as AS IL-4 failed to inhibit virus replication (data not shown).

EXAMPLE 3

Modulation of IL-4 and CXCR4 RNAs by Exogenous IL-4 and AS IL-4 ODN

To explore whether the enhancing effect of IL-4 was associated with modulation of endogenous IL-4 production, and whether AS ODN designed against IL-4 truly inhibited endogenously produced IL-4 in treated cultures, an IL-4 specific RT-PCR analysis of RNA extracted from infected cultures that were treated with IL-4 and AS IL-4 DNA was performed.

Following 24 hours of treatment, cellular RNA was extracted by Trizol, DNAse treated and assessed for IL-4 mRNA levels. As shown in the FIG. 3A, infected macrophages treated with IL-4 showed a marked increase in IL-4 mRNA while cultures treated with AS IL-4 showed significantly reduced levels of IL-4 mRNA.

Figure 3:
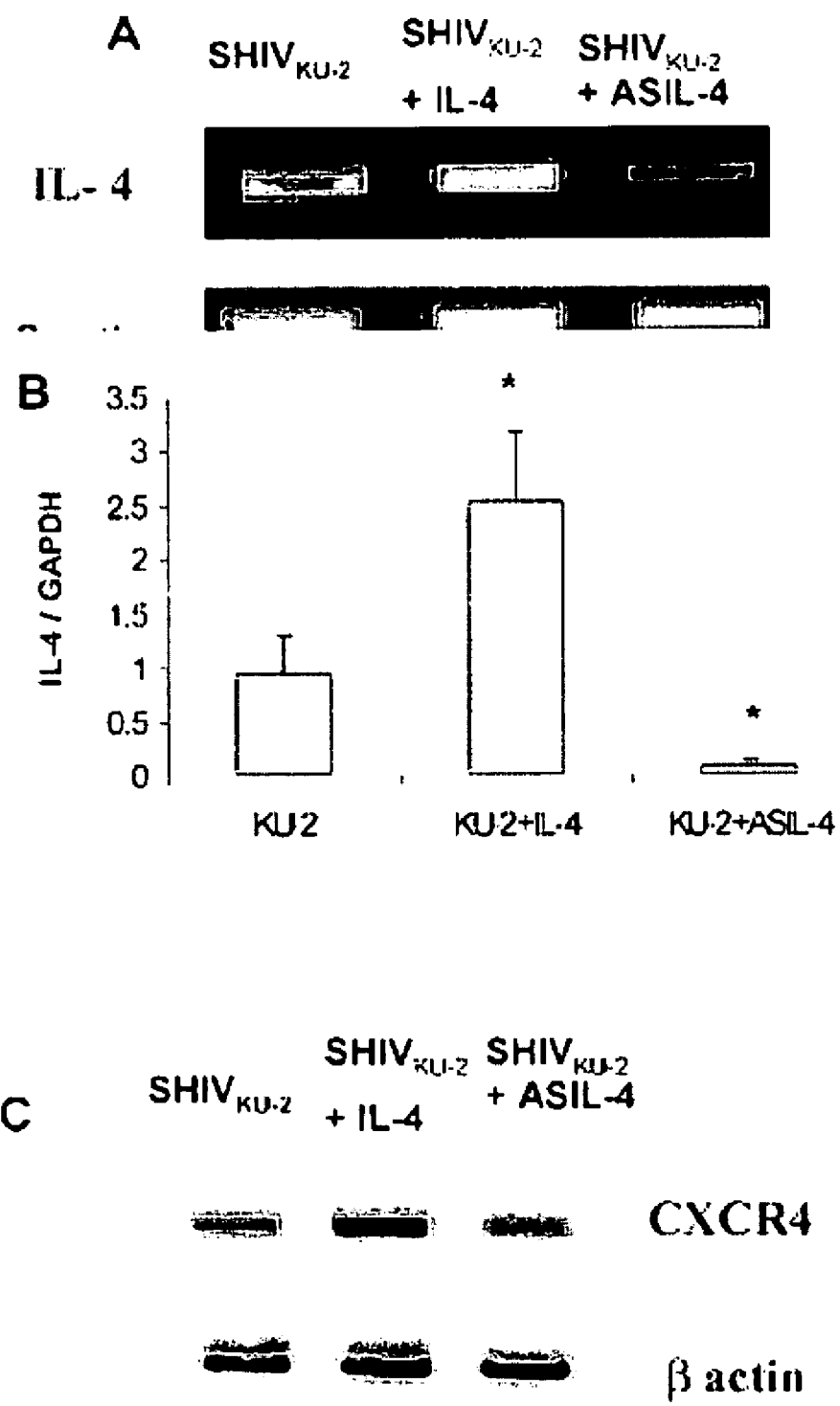
FIG. 3A-B illustrates the levels of IL-4 mRNA in $SHIV_{KU-2}$-infected $CD4^+$ T cells treated with rmIL-4 or AS IL-4 as seen by RT-PCR (panel A) and quantitative real time RT-PCR (panel B).
FIG. 3C shows the RT-PCR analysis of CXCR4 mRNA in $SHIV_{KU-2}$ infected MDM in the presence of rmIL-4 or AS IL-4 ODN using macaque CXCR4 primers.

These findings were confirmed by real time RT-PCR (FIG. 3B). FIG. 3B represents a ratio of IL-4 and GAPDH RNA transcripts. The * indicates a P value<0.05 compared to SHIV infected cells.

It was previously shown that the virus-enhancing effect of IL-4 correlated with increased expression of the viral co-receptor, CXCR4 in treated cultures (Valentin 1998, Hicks 2002, Wang 1998). As shown in FIG. 3C, analysis of CXCR-4 message by RT-PCR demonstrated a down regulation of CXCR4 mRNA in SHIV infected $CD4^+$ T cells treated with AS IL-4 ODN as opposed to an up-regulation in IL-4 treated cultures, emphasizing the specificity of the AS IL-4 effect.

EXAMPLE 4

SHIV Replication in the Presence of Sense and Antisense IL-4 Plasmid DNA

AS IL-4 ODNs provided a tool to assess the role of endogenously produced IL-4 on SHIV replication. The observed inhibition of virus replication in virus-infected cultures of lymphocytes and macrophages by AS IL-4 ODNs suggested that this mechanism may provide a novel therapeutic approach. However, because of the prohibitive cost of ODNs, the present invention explored whether recombinant AS IL-4 DNA could be substituted to synthetic ODNs for the purpose of inhibiting endogenous IL-4 production.

Plasmids expressing AS or sense IL-4 were constructed, propagated in bacteria, and transfected into virus-infected macrophages using the cationic lipid, in vitro jet-PEI-Man (Qbiogene). SHIV infection was then monitored by RT activity at different time intervals.

Figure 4:
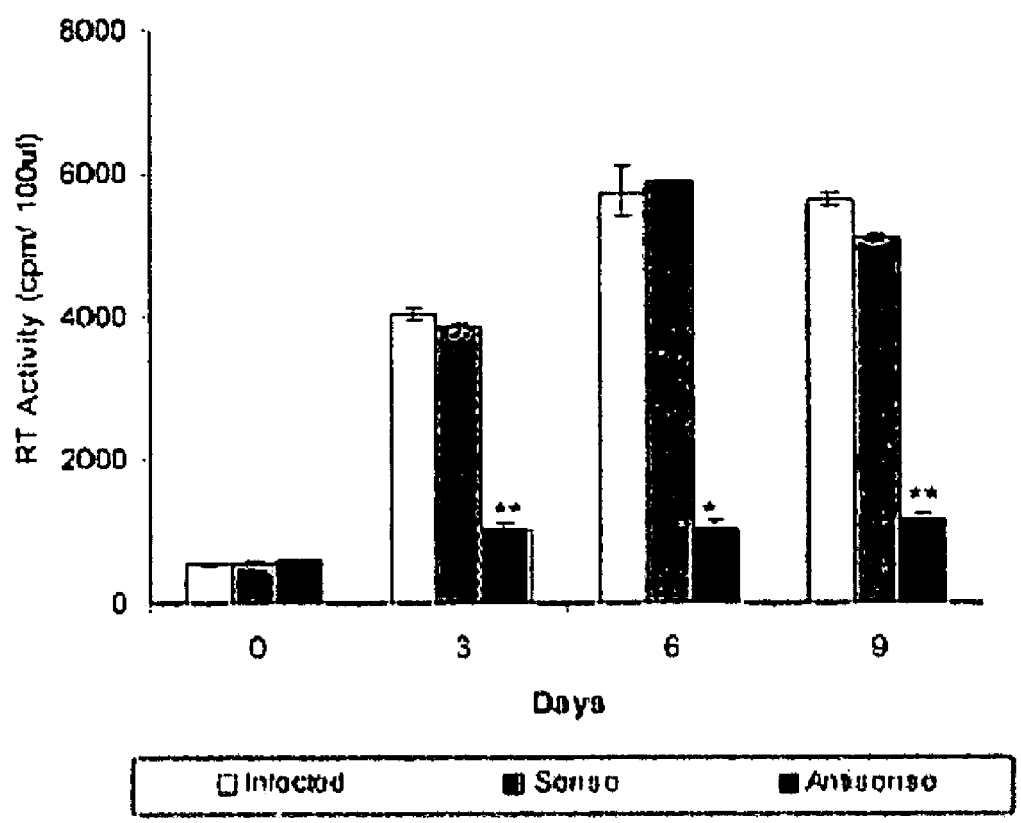
FIG. 4 shows $SHIV_{89.6}P$ replication in macrophages in the presence of sense and AS IL-4 plasmids. The "*" indicates a P value<0.01, and "**", a P value<=0.001, compared to control infected cultures.

As shown in FIG. 4, a single treatment of the infected cultures with AS IL-4 resulted in marked and sustained reduction of virus replication by as much as 85% for the next nine days. In contrast, no significant inhibition of virus replication was observed in control cultures administered a sense IL-4 plasmid. These results confirmed that the AS IL-4 expressing vector had the same effect as the ODNs and therefore could be substituted for the latter in therapeutic attempts.

EXAMPLE 5

Biodistribution of GFP in Macaque Tissues

No data is currently available on the biodistribution of liposome-mediated plasmid delivery via the intravenously route in macaques. This example involved the an experiment to address the biodistribution of liposomes containing the GFP reporter gene in macaque tissues and showed that the reporter transgene was concentrated in the major clearance organs of the body, namely the liver, lungs and spleen.

More specifically, as a preliminary investigation prior to IV delivery of AS IL-4 to infected macaques, the biodistribution of a reporter gene, green fluorescent protein (GFP), was examined in one macaque. The animal was injected IV with the GFP plasmid and killed two days later. Tissues were collected, fixed, and the frozen sections examined to visualize distribution using confocal microscopy.

Figure 5:
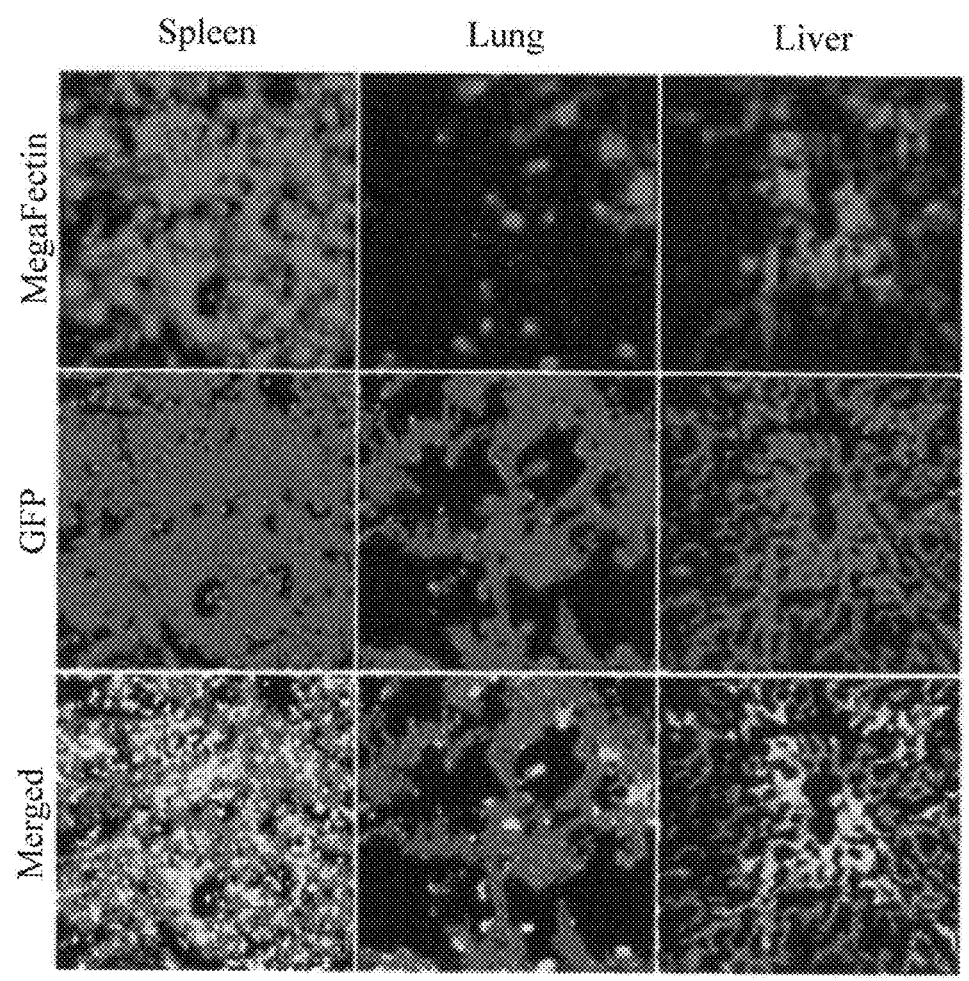
FIG. 5 shows the co-localization of GFP (green) and in vivo MegaFectin complexes (red) in the spleen (A), lungs (B) and liver (C) of a macaque.

As shown in FIG. 5, direct visualization of fixed tissue sections using confocal microscopy revealed co-localization of MegaFectin (red fluorescence) and GFP (green fluorescence) in lungs, liver and spleen. These three organs are primarily involved in the clearance of particulate foreign matter from the blood. This experiment was a prerequisite for additional experiments using liposomes containing AS IL-4 DNA as a therapy for infected macaques.

EXAMPLE 6

Inhibition of Virus Replication in Macaques Treated with Liposomes Containing AS IL-4 DNA Having determined that IV administration of liposomes would be cleared from blood by cells in the liver, lungs, and spleen, these tissues coincidentally being the site of virus replication predominantly in macrophages, this example investigated whether AS IL-4 would inhibit virus replication in these organs in vivo.

In this example, monkeys were treated with AS IL-4 DNA during the acute phase of SHIV infection as significant levels of systemic viral replication are observed during the first 2 to 4 weeks post infection. The animals were therefore inoculated with $SHIV_{89.6}P$; two were given AS IL-4 on day 7 post-infection, and two others received the AS IL-4 on days 7 and 9 post-infection. The two virus control animals were not treated. All six animals were killed at two weeks post-infection. Blood from the four treated and two untreated animals was analyzed on days 7, 10 and 14 for viral RNA content in plasma, and $CD4^+$ T cell counts in the mononuclear cells in peripheral blood. The rationale for giving AS treatment one week following virus inoculation was based on the fact that the virus causes massive infection with peak viremia in cynomolgus macaques by one week following IV injection of the virus. The scale of the infection in the macaques exceeds by far the severity of HIV infection in humans, thus emphasizing the efficacy of the treatment described below.

Figure 6A:
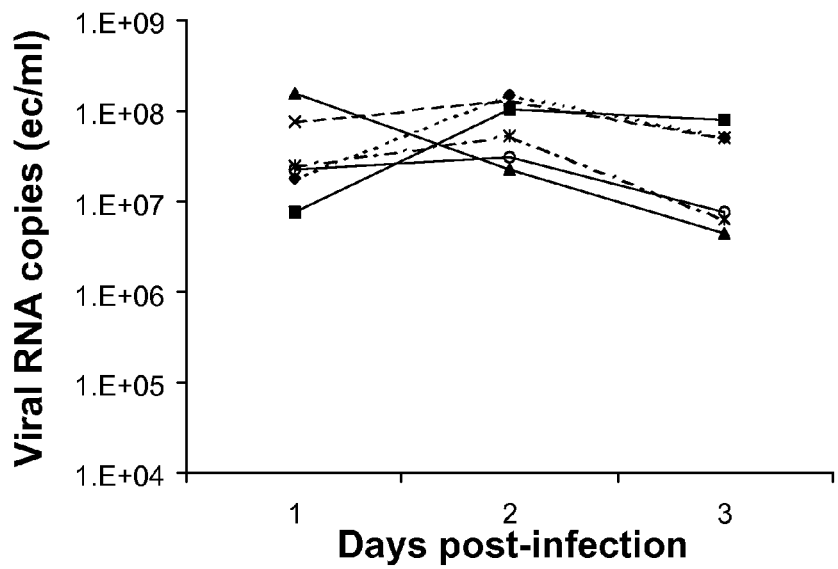
FIG. 6A graphically illustrates the cell-free plasma viral RNA load of the treated (one or two treatments) and untreated macaques at multiple time points as determined by real time RT-PCR using standards covering six orders of magnitude. Viral loads are shown as viral RNA copies/ml of plasma.
Figure 6B:
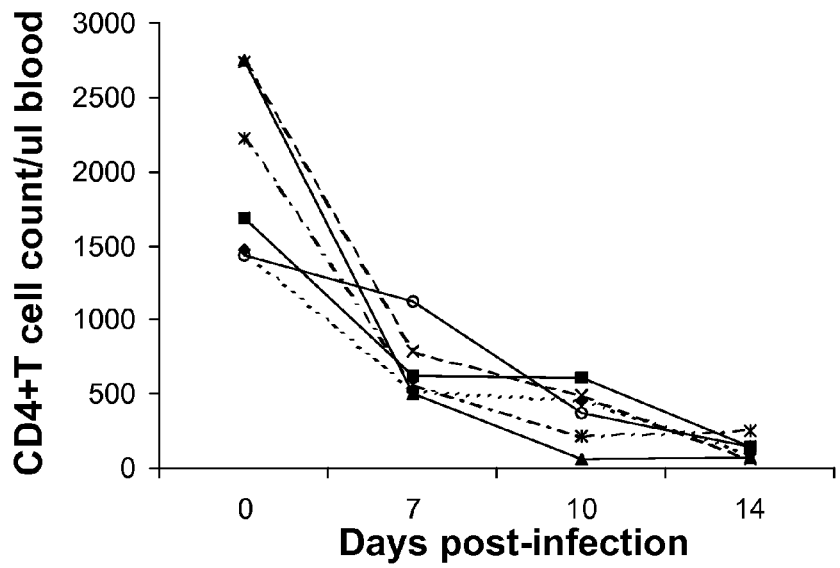
FIG. 6B shows the $CD4^+$ T cell profile in the control and AS IL-4-treated $SHIV_{89.6}P$-infected macaques. The absolute number of $CD4^+$ T cells/μl of blood were calculated by multiplying the percentage of lymphocyte subset with the absolute number of lymphocytes/μl from complete blood count.
Figure 6B:
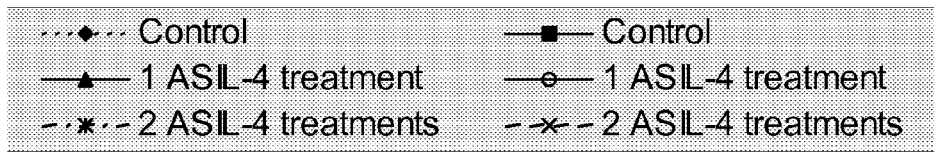

FIG. 6A shows that by day 7 post-inoculation, all six animals had viral RNA concentrations varying from $10^7$ to $10^8$ copies/ml plasma. Titers remained essentially at this level by day 10 and declined slightly by day 14. In three of the four AS IL-4-treated animals, there was a one log 10 reduction in the plasma viral RNA concentration compared to the control animals. $CD4^+$ T cell numbers declined precipitously in both the treated and untreated animals following virus inoculation, as shown in FIG. 6B. There was no significant difference between the $CD4^+$ T cell counts from the control or treated animals.

Tissue samples of organs in which the AS IL-4 DNA was expected to accumulate were examined for virus content. Liver, lung and splenic tissues from the four treated and the two untreated infected macaques were examined for presence of full length viral gag mRNA by real time RT-PCR. Gag RNA copy numbers were normalized to the copy number of the cellular mRNA for HPRT, also measured by real time RT-PCR. Viral RNA and immunohistochemical analyses of tissues from the untreated infected animals showed intense replication of virus in the three tissues. These findings were matched by significantly less viral RNA and viral antigen concentrations in all three tissues from the four animals that were given the AS IL-4 DNA. The gag/HPRT ratio showed that the tissues from treated animals exhibited markedly less viral RNA than those of the two control animals.

Figure 7A:
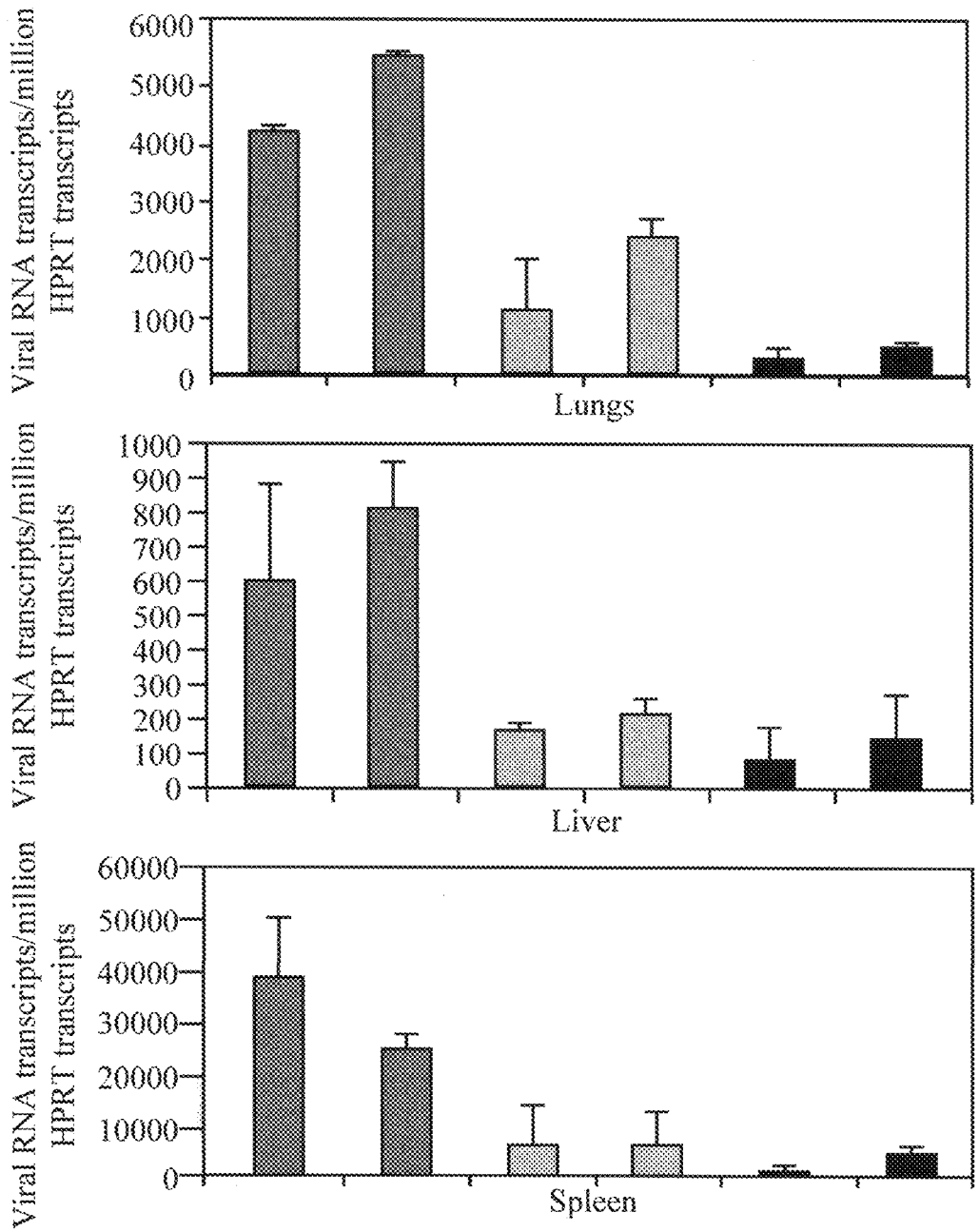
FIG. 7A-B shows the viral RNA load in AS IL-4 treated and untreated SHIV infected macaques as seen by real-time RT-PCR and immunohistochemistry.

Further, as shown in FIG. 7A, the tissues from the two animals that received two injections of liposome/AS IL-4 DNA had even less viral RNA than the two that received only a single treatment. Specifically, animals receiving a single injection of AS IL-4 had 60% less viral RNA, whereas the two that were treated twice had about 80-90% reduction in the viral RNA in spleen and lung compared to the two untreated controls.

Figure 7B:
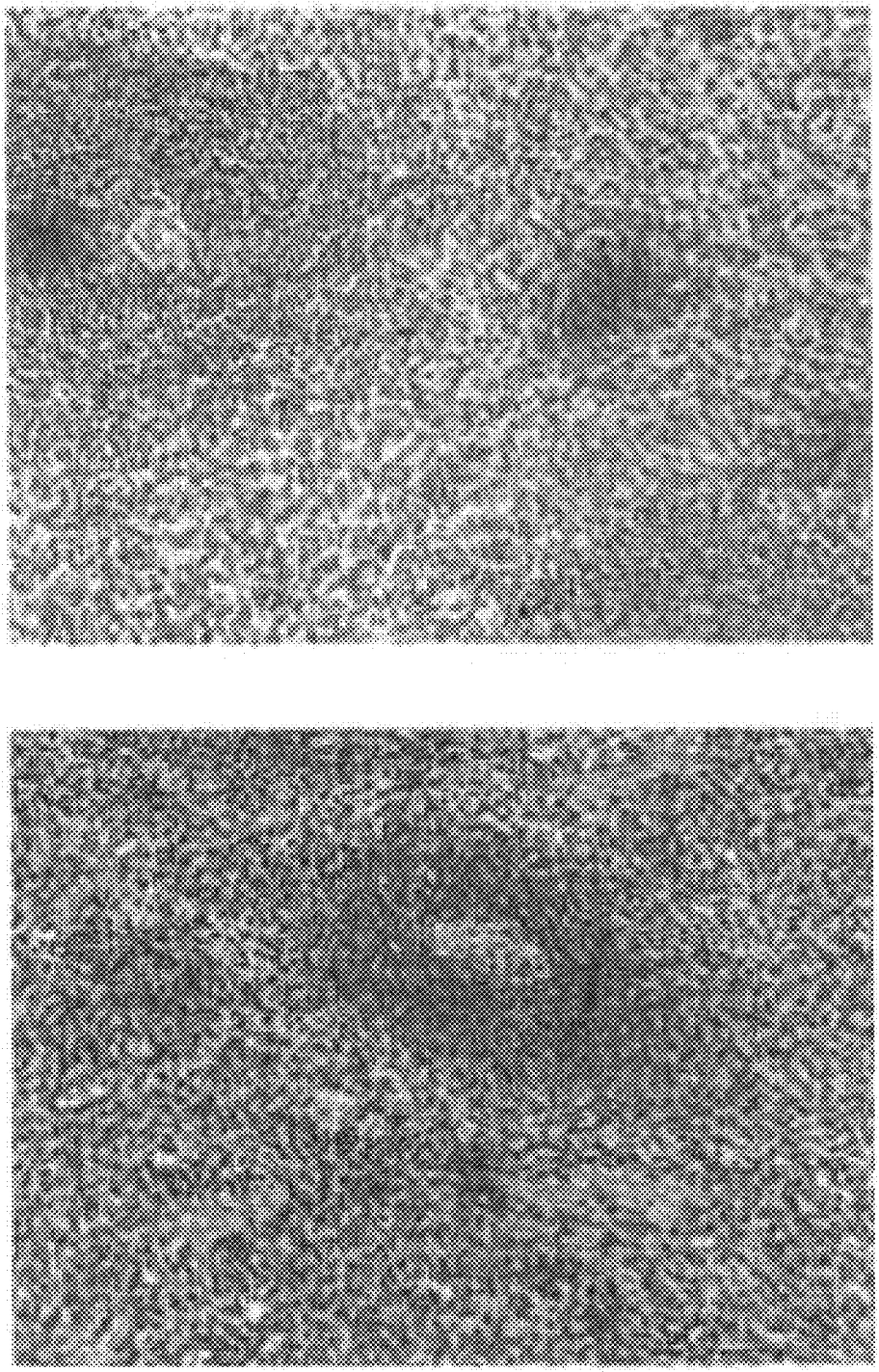

Immunohistochemical studies on spleen sections using a Gag specific antibody corroborated the viral RNA quantification data since only a few small foci of viral-infected cells were found in the tissue sections of the AS treated animals compared to many large foci of viral antigen-positive cells in splenic sections of the untreated animals (FIG. 7B). The virus-positive cells in the spleen were primarily macrophages in the red pulp area of the spleen (data not shown).

EXAMPLE 7

Induction of Cell-Mediated Immune Response in Lymph Nodes

It is thought that the progressive loss of CD4+ T cells eventually results in loss of the CMI responses including IFN-gamma-mediated cytotoxic T lymphocyte ("CTL") function, thereby creating a rich environment for proliferation of opportunistic pathogens. Many of these pathogens exhibit a strong Th2 response, resulting in production of cytokines such as IL-4. IL-4 in turn promotes replication of mutant phenotypes of HIV that utilize the X4 co-receptor by causing enhancement of expression of this chemokine receptor (Hicks 2002,Valentin 1998) and CD4+ (Wang 2002). The X4 viruses replicate lytically in naïve CD4/X4 T cells, evident by rapid disappearance of CD4+ T cells from the blood, thereby accelerating the demise of the adaptive CMI response system.

Knowing the antagonistic relationship between Th1 and Th2 responses in induction of cell-mediated immune responses ("CMI"), the data from Example 6 was reevaluated. More specifically, although the demise of the initial IFN-gamma-mediated Th1 response is largely attributable the viral elimination of CD4+ T cells, this example investigated whether that observation could have been accelerated by early induction of the Th2 cytokine IL-4 that would further suppress the CMI response. Was this the case, the latter effect would be expected to be more global in the animals beyond the three clearance organs from Example 6.

Figure 8A:
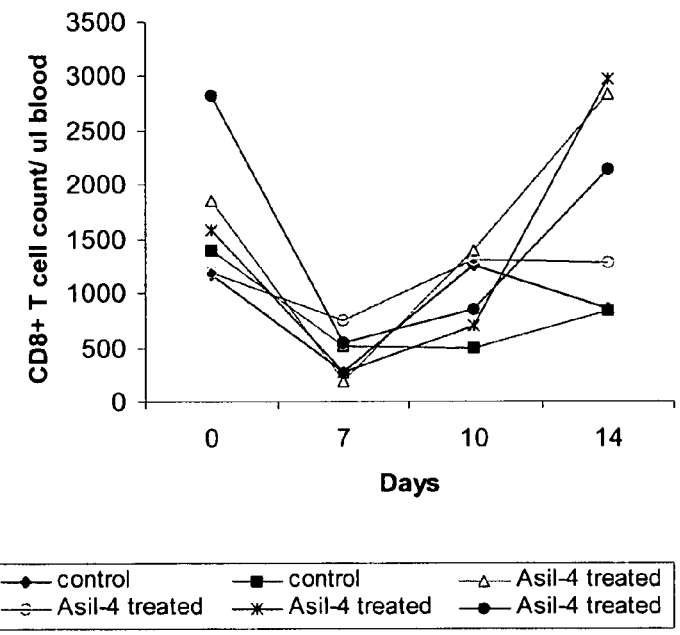
FIG. 8 shows the $CD^+8$ T cell profile in the control and AS IL-4 treated $SHIV_{89.6}P$-infected macaques (FIG. 8A) and mean fluorescence intensity of $CD8^+$ T cells (FIG. 8B).
Figure 8B:
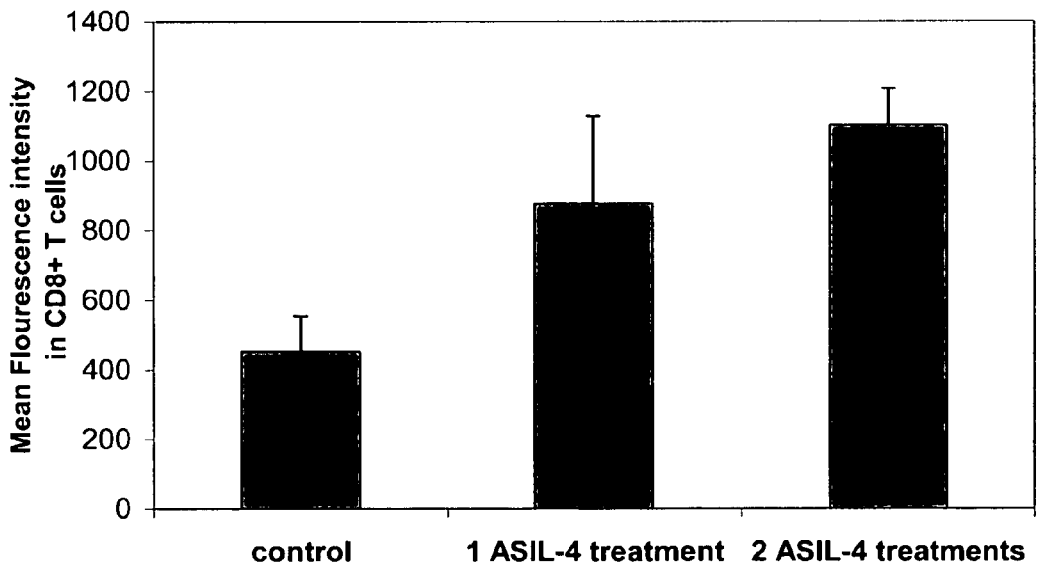

More specifically, this example investigated whether the activity of CD8+ T cells, the mediators of CMI responses, were affected by the AS IL-4 DNA treatment. PBMC from the infected animals treated with AS IL-4 DNA was investigated for CD4+ and CD8+ T cells by FACS on 7, 10 and 14 days post-infection. FIG. 8A shows that there was significant increase in the CD8+ T cells in blood from all four of the treated, compared to the untreated infected animals. Similarly, an increase was observed when the MFI of CD8+ was investigated (FIG. 8B) suggesting that CD8 expression was indeed increased in CD8+ T cells of the treated animals. It was assumed that this increase in the treated animals was due to inhibition of IL-4 by AS IL-4.

Figure 9A:
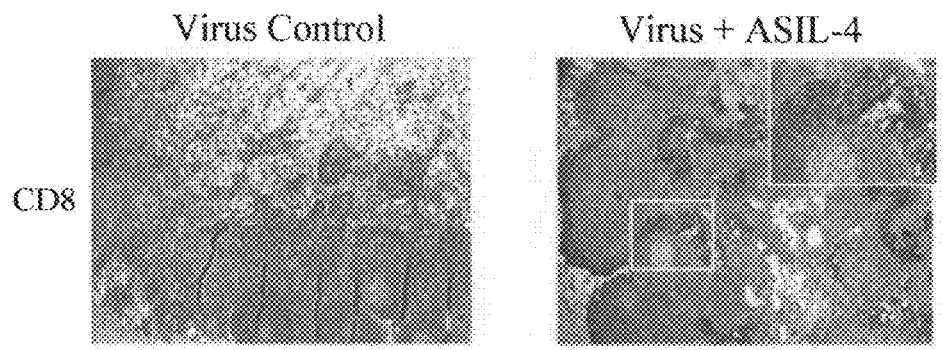
FIG. 9 shows the proliferation and activation of $CD8^+$ T cells in lymph nodes of infected macaques treated with AS IL-4. Immunohistochemistry for CD8 (FIG. 9A) and granzyme B (FIG. 9B) in mesenteric lymph node paraffin embedded sections is shown. Immunohistochemical results for lymph nodes from untreated control animals that are severely depleted due to infection caused by X4 viruses is shown FIG. 9C.
Figure 9B:
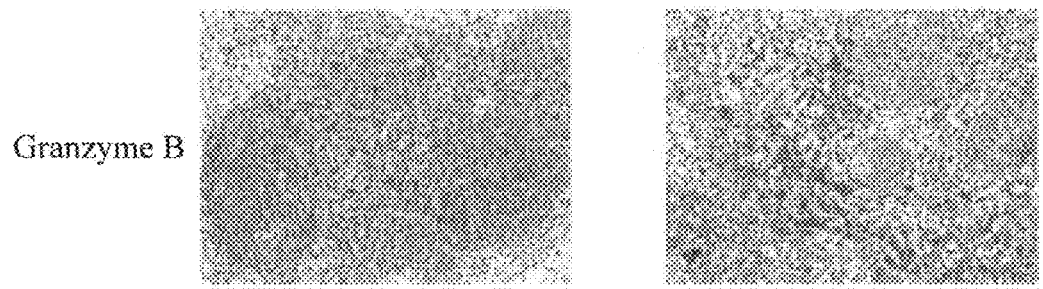
Figure 9C:
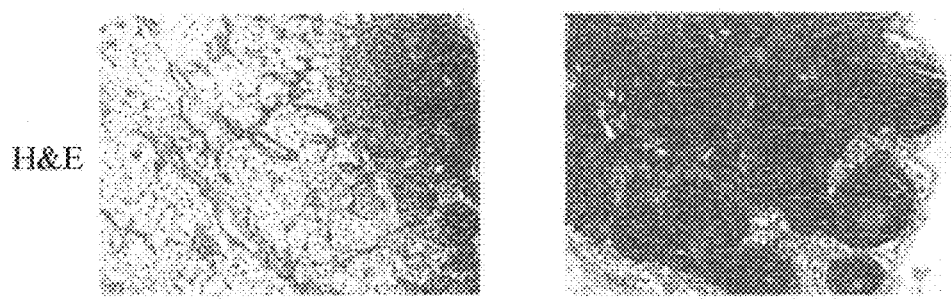

This example also investigated whether CD8+ T cells had proliferated in lymph nodes and whether there was increased granule cytotoxicity of CD8+ T cells due to increase granzyme synthesis since IL-4 is thought to prevent both effects (Villacres 1999; Kienzle 2002). As shown in FIG. 9A, immunohistochemical analysis showed that CD8+ T cell numbers were dramatically increased in the lymph nodes of the treated animals compared to the nodes from the two control animals. An increase in CD8+ cells in the lungs and spleen of treated animals was also observed (data not shown). Further, as shown in FIG. 9B, using expression of granzyme as a marker of activation, this example showed that much larger numbers of granzyme-positive cells were present in the nodes of the treated animals compared to the control animals. The nodes were in a better state of preservation compared to the untreated control animals in which the nodes were already severely depleted, as is typical in infections caused by these X4 viruses (FIG. 9C).

Figure 10A:
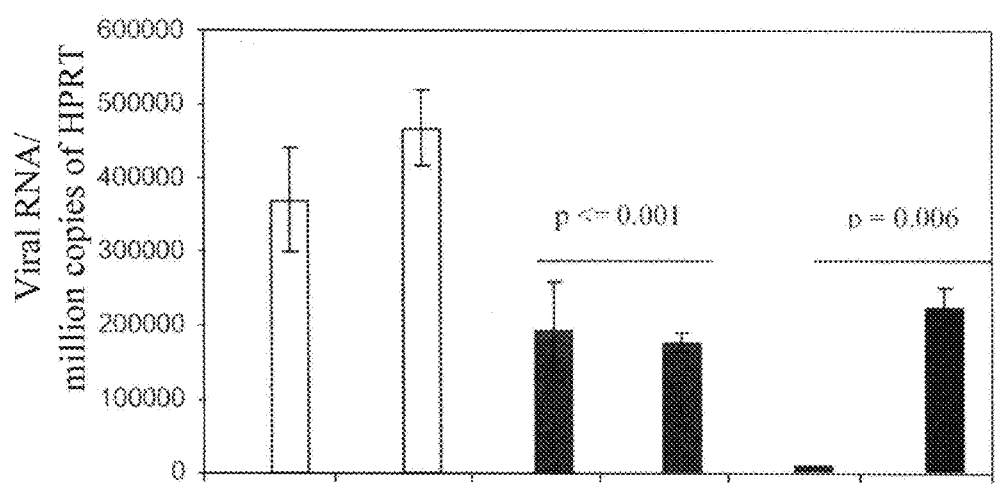
FIG. 10A shows the viral load in mesenteric lymph node ("MLN") of AS IL-4 DNA treated and untreated SHIV infected macaques as seen by real-time RT-PCR. The lighter first set of bars indicates viral RNA levels MLN in the $SHIV_{89.6}P$-infected macaques. The medium-shaded second set of bars indicates viral RNA, in infected macaque with a single dose of AS IL-4, and the third darkest set of bars indicates viral RNA in the animals receiving two injections of the AS IL-4. Viral gag mRNA/HPRT ratios obtained after real-time RT-PCR are presented. RNA was extracted from three different regions of each tissue and analyzed individually.
Figure 10B:
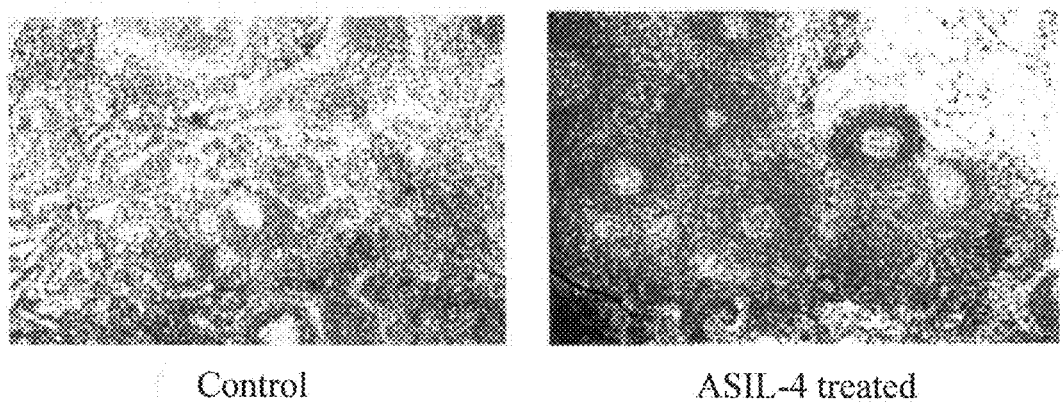
FIG. 10B shows the p27 staining in the mesenteric lymph node sections of control (left panel) and animals treated with AS IL-4 (right panel).

Tests for virus replication showed a significant drop in the copies of viral RNA in mesenteric and peripheral lymph nodes of all the four treated compared to the untreated animals (FIG. 10A). In addition, immunohistochemical staining for viral gag protein confirmed the lower viral load in the lymph nodes of the treated macaques. Increased numbers of viral foci were seen in the sections from control infected animals (FIG. 10B). However, ELISPOT analysis of PBMC, the only live cells that were saved from the animals, showed that there was no significant difference in the numbers of cells producing IFN-gamma. It is possible that the activated cells in the nodes had not yet migrated into the blood.

Decreased viral antigen expression in the mesenteric and peripheral lymph nodes of the treated animals as well as decreased viral RNA concentrations in the plasma data correlated well with increase in CD8+ T cell proliferation and activation. Further, the treated animals had better preservation of lymph node architecture than the virus control animals. These data suggested that although all of the animals had already developed severe depletion of peripheral CD4+ T cells, they did develop CMI responses that were suppressed by IL-4 whose effects increased in concert with the decreasing numbers of naive and activated CD4 T cells. The data suggest that the AS IL-4 rescued the CMI response, which once activated, may have caused the observed decrease in viral replication, and prevented further destruction of the nodes.

EXAMPLE 8

Construction of a DNA Immunogenic Composition Including AS IL-4

In this example, the AS IL-4 was incorporated into a DNA-based vaccine. The construct could theoretically concomitantly inhibit of the expression of IL-4 and also provide SHIV DNA immunization to enhance the specific CMI response. More specifically, the vaccine described in Narayan et al., U.S. patent application Ser. No. 10/941,164 filed on Sep. 15, 2004 entitled "DNA Vaccine Compositions and Methods of Use" ($\Delta$4-SHIV$_{KU-2}$ vaccine genome), which is incorporated by reference, was used to remove the coding sequences for the accessory protein Vpr to generate a construct known $\Delta$5-SHIV$_{KU-2}$ and to replace them with those expressing the AS DNA of the host. Preliminary experiments involved introduction of the AS IL-4 gene from the mouse. The mouse IL-4 sequence is disclosed in Noma et al., Cloning of cDNA Encoding the Murine IgG1 Induction Factor by a Novel Strategy using SP6 Promotor, Nature 319 (6066), 640-66 (1986) and Lee et al., Isolation and Characterization of a Mouse Interleukin cDNA Clone that Expresses B-Cell Stimulatory Factor Activities and Mast-Cell-Stimulating Activities, Proc. Natl. Acad. Sci. USA 83 (7), 2061-65 (1986), which are incorporated by reference. The resulting recombinant plasmid was named $\Delta$5-SHIV$_{KU-2}$-AS-mIL-4. It will be appreciated that the type of AS IL-4 used in the vaccine will ultimately depend upon the host organism. That is, analogues constructs for macaque and human administration will involve AS IL-4 from the macaque and human genome, respectively.

More specifically, $\Delta$4-SHIV$_{KU-2}$ DNA was digested with Nco-1 and Xba-1 to release the sequences coding for Vpr at 3594 and 3713, known as $\Delta$5-SHIV$_{KU-2}$ DNA. The 9675 bp large DNA fragment was gel-purified and used to insert the AS-IL-4 sequences.

Figure 11:
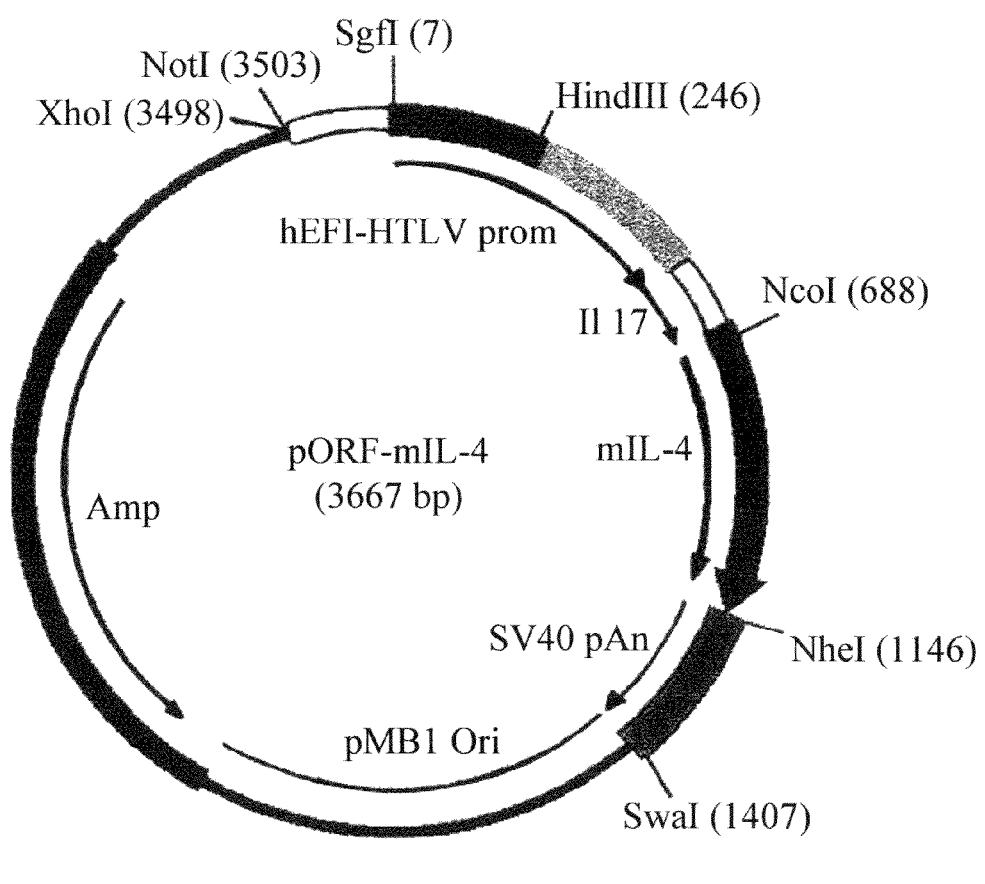
FIG. 11 illustrates the Invivogen mouse IL-4 ("mIL-4") expression plasmid DNA used to construct an AS IL-4 plasmid in conjunction with the present invention.
Figure 12:
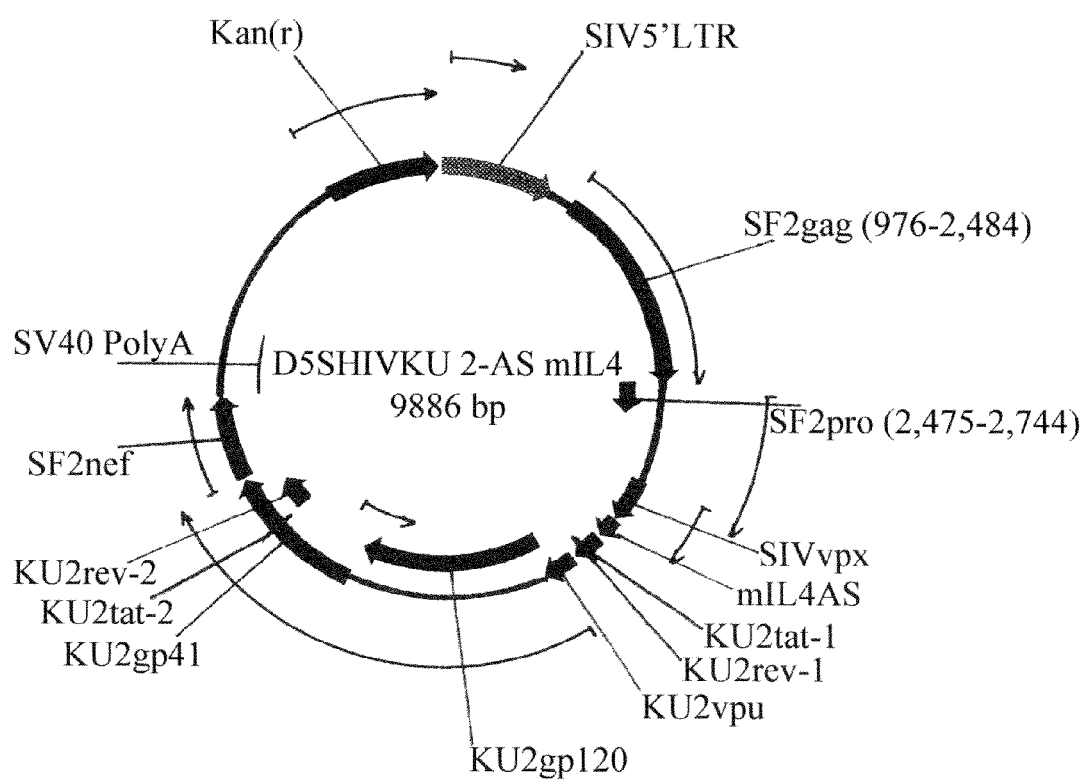
FIG. 12 is a circular diagram of a DNA immunogenic construct of the present invention, which incorporates AS IL-4 in place of the vpr gene of $\Delta 4\text{-}SHIV_{KU-2}$ to create $5\text{-}SHIV_{KU-2}\text{-}ASIL\text{-}4$ DNA.
Figure 13:
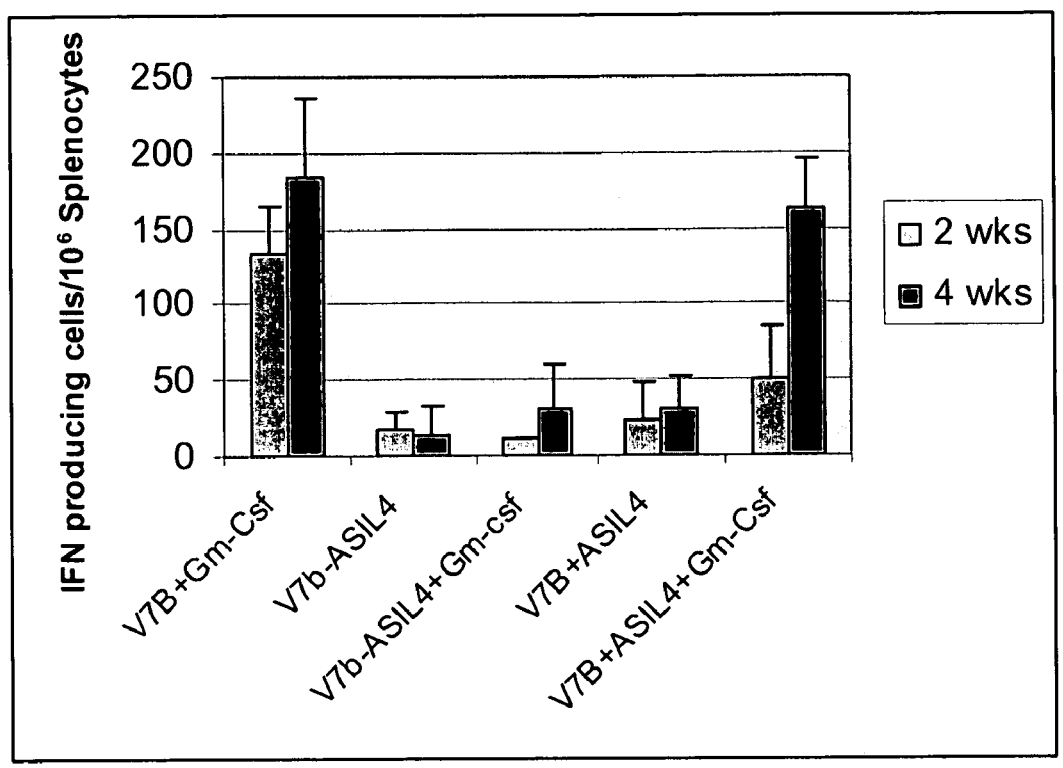
FIG. 13 shows the IFN-gamma-mediated cytotoxic T lymphocyte ("CTL") response of mice immunized with (1) 200 μg of $\Delta 4\text{-}SHIV_{KU-2}$ DNA and 100 μg of GM-CSF DNA (control); (2) 200 μg of $\Delta 5\text{-}SHIV_{KU-2}\text{-}ASIL\text{-}4$ DNA; (3) 200 μg of $\Delta 5\text{-}SHIV_{KU-2}\text{-}ASIL\text{-}4$ DNA and 100 μg of GM-CSF DNA; (4) 200 μg of $\Delta 4\text{-}SHIV_{KU-2}$ DNA and 100 μg of AS IL-4 DNA, and (5) 200 μg of $\Delta 4\text{-}SHIV_{KU-2}$ DNA, 100 μg of AS IL-4 DNA, and 100 μg GM-CSF DNA.

Next, the pORF-mIL-4 expression plasmid DNA commercially provided by Invivogen (San Diego, Calif.), and carrying the full coding sequences of mouse IL-4 (mIL-4), see FIG. 11, was used to amplify a PCR product using MIL-4-5 (SEQ. ID NO. 7: 5'-cca tgg ata tgc gaa gca cct-3' located at positions 216-232 of the IL-4 gene and 906-920 in the plasmid map) and mIL-4-1 (SEQ. ID NO. 8: 5'-ggc tag cac ttg aga gag atc atc-3' located at position 85-102 of the IL-4 gene and 773-790 in the plasmid map) oligonucleotide primers to generate a 155 base pair fragment from the central part of the IL-4 gene having unique Nco1 and Nhe1 sites at its extremities. This PCR product was double digested with Nco-1 and Nhe-1, purified and ligated in the opposite transcriptional direction into the 9675 bp Nco-1/Xba-1 Δ5-SHIV$_{KU-2}$ DNA fragment previously prepared above. Ligated DNA was introduced into JM-109 bacteria and recombinant colonies were screened to isolate the recombinant vector having the expected insert. The resulting final DNA construct was named Δ5-SHIV$_{KU-2}$-AS-mIL-4, which is illustrated in FIG. 12.

EXAMPLE 9

Investigation of Δ5-SHIV$_{KU-2}$-AS-mIL-4 and/or GM-CSF, and AS IL-4 Co-Administered with Δ4-SHIV$_{KU-2}$ and/or GM-CSF In this example, the effect of AS IL-4 on in vivo viral replication was investigated. Five groups of 8 mice each were used in this experiment. The first group was immunized with 200 μg of Δ4-SHIV$_{KU}$-2 DNA and 100 μg of GM-CSF DNA (control). The second group was immunized with 200 μg of Δ5-SHIV$_{KU-2}$-AS-mIL-4 DNA from Example 8. The third group were immunized with 200 μg of Δ5-SHIV$_{KU-2}$-AS-mIL-4 DNA from Example 8 and 100 μg of GM-CSF DNA. The fourth group were immunized with 200 μg of Δ4-SHIV$_{KU-2}$ DNA and 100 μg of AS IL-4 DNA having SEQ. ID No. 1. The last group was immunized with 200 μg of Δ4-SHIV$_{KU-2}$ DNA and 100 μg of AS IL-4 DNA having SEQ. ID No. 1 and 100 μg GM-CSF DNA (Invitrogen). Four mice from each group were euthanized at 2 and 4 weeks post immunization and examined for the cellular immune response by ELISPOT assay. The ELISPOT values obtained with mice from each group at week 2 and 4 are used to plot the diagram that is represented in the figure. These data show a loss of ELISPOT response of Δ4-SHIV$_{KU-2}$ when the antisense IL-4 is introduced in the genome (Δ5-SHIV$_{KU-2}$-AS-mIL-4). This loss is not restored by the combination with the GM-CSF at week 2 and mildly restored at week 4. Similarly, the combination of Δ4-SHIV$_{KU-2}$ DNA with AS IL-4 DNA induced inhibition of Δ4-SHIV$_{KU-2}$ induced ELISPOT response at both 2 and 4 weeks, that was partially restored with GM-CSF at 2 weeks and completely restored at 4 weeks post immunization. Thus, the use of cytokines and adjuvants such as GM-CSF in conjunction with the AS IL4 of the present invention are contemplated to have a beneficial effect.

In sum, in the present invention, the SHIV model was used to show that AS IL-4 could inhibit virus replication in tissue macrophages in vivo. The present invention also takes advantage of the fact that macrophages in the liver, lungs, and spleen become predominant host cells for virus replication following elimination of CD4$^+$ T cells. Part of the novelty of the approach used in the present study was that the AS IL-4 was directed to a host factor that regulates virus replication. The therapy was highly effective in curtailing virus replication in tissues in which macrophage-tropic virus replication is known to occur. Thus, targeting of AS IL-4 plasmid may be used in future therapeutic attempts as adjunct therapy for defined and organ specific symptoms caused by virus replication in the macrophages. One such organ could be the brain. These small inhibitory molecules may not only be effective in macrophages in systemic tissues, but may also have a better chance of crossing the blood brain barrier than the antiretroviral drugs currently in use, with the potential for quelling virus replication in macrophages in the brain.

In the successful therapy of SHIV-infected animals with AS IL-4, one of the mechanisms was probably reduction of availability of target cells of the virus by means of reduction of CD4 and CXCR4, the co-receptor used by the virus in cells in the clearance organs, lungs, liver, and spleen. However, a second mechanism was the possible negation of the immunological function of IL-4 since the therapeutic effect of the AS-IL-4 treatment appeared to rescue the antiviral CD8$^+$ T cell response. This response must have been induced in the very early stage of the infection, but expansion of the effector-activated cells was inhibited by IL-4, in exertion of its normal physiological function. The net effect of this is the well-known lack of CMI responses in SHIV infected with acute loss of CD4$^+$ T cells. CMI responses do develop during the acute disease and can be rescued by administration of AS IL-4. Still another possible mechanism is that the AS IL-4 DNA induced siRNA in the tissues, and the siRNA molecules in turn caused the global antiviral effect in the tissues. Regardless of the mechanism, this provides strong support for inclusion of this DNA as an adjunct therapy for HIV infections.

Lastly, a number of DNA ODNs against several regulatory and structural (Weichold 1995, Kim 1995, Mautino 2000, Morris 2004), gene products of the virus have been designed as anti-HIV therapeutic agents. This approach, however, has limited clinical feasibility because of the high mutation rate of the HIV genome and the genetic variation between different strains of the virus (Brenner 2002). The present invention differs from such an approach in that it targets the host immune response.

All publications mentioned herein are incorporated herein by reference to describe the methods and/or materials in connection with which the publications are cited.

(1) Rosenberg Z F, Fauci A S. Immunopathology and pathogenesis of human immunodeficiency virus infection. Pediatr Infect Dis J. 1991;10:230-238.

(2) Pantaleo G, Graziosi C, Fauci A S. The Immunopathogenesis of Human-Immunodeficiency-Virus Infection. New England Journal of Medicine. 1993;328:327-335.

(3) Ho D D, Neumann A U, Perelson A S et al. Rapid turnover of plasma virions and CD4 lymphocytes in HIV-1 infection. Nature. 1995;373:123-126.

(4) Igarashi T, Brown C R, Endo Y et al. Macrophage are the principal reservoir and sustain high virus loads in rhesus macaques after the depletion of CD4$^+$ T cells by a highly pathogenic simian immunodeficiency virus/HIV type 1 chimera (SHIV): Implications for HIV-1 infections of humans. Proc Natl Acad Sci USA. 2001;279.

(5) Orenstein J M, Fox C, Wahl S M. Macrophages as a source of HIV during opportunistic infections. Science JID—0404511. 1997;276:1857-1861.

(6) Igarashi T, Imamichi H, Brown C R, Hirsch V M, Martin M A. The emergence and characterization of macrophage-tropic SIV/HIV chimeric viruses (SHIVs) present in CD4$^+$ T cell-depleted rhesus monkeys. J Leukoc Biol. 2003; 74:772-780.

(7) Harms G, Feldmeier H. HIV infection and tropical parasitic diseases—deleterious interactions in both directions? Trop Med Int Health. 2002;7:479-488.

(8) Orenstein J M. The macrophage in HIV infection. Immunobiology. 2001;204:598-602.

(9) Pal R, Taylor B, Foulke J S et al. Characterization of a simian human immunodeficiency virus encoding the envelope gene from the CCR5-tropic HIV-1Ba-L. Jaids—Journal of Acquired Immune Deficiency Syndromes. 2003;33:300-307.

(10) Chen Z, Huang Y, Zhao X et al. Enhanced infectivity of an R5-tropic simian/human immunodeficiency virus carrying human immunodeficiency virus type 1 subtype C envelope after serial passages in pig-tailed macaques (*Macaca nemestrina*). J Virol. 2000;74:6501-6510.

(11) Liu Z Q, Muhkerjee S, Sahni M et al. Derivation and biological characterization of a molecular clone of SHIV$_{(KU-2)}$ that causes AIDS, neurological disease, and renal disease in rhesus macaques. Virology. 1999;260:295-307.

(12) Igarashi T, Donau O K, Imamichi H et al. Macrophage-tropic simian/human immunodeficiency virus chimeras use CXCR4, not CCR5, for infections of rhesus macaque peripheral blood mononuclear cells and alveolar macrophages. Journal of Virology. 2003;77:13042-13052.

(13) Valentin A, Lu W, Rosati M et al. Dual effect of interleukin 4 on HIV-1 expression: implications for viral phenotypic switch and disease progression. Proc Natl Acad Sci USA JID—7505876. 1998;95:8886-8891.

(14) Reimann K A, Li J T, Veazey R et al. A chimeric simian/human immunodeficiency virus expressing a primary patient human immunodeficiency virus type 1 isolate env causes an AIDS-like disease after in vivo passage in rhesus monkeys. J Virol. 1996;70:6922-6928.

(15) Joag S V, Li Z, Foresman L et al. Characterization of the pathogenic KU-SHIV model of acquired immunodeficiency syndrome in macaques. AIDS Res Hum Retroviruses. 1997; 13:635-645.

(16) Sui Y, Potula R, Pinson D et al. Microarray analysis of cytokine and chemokine genes in the brains of macaques with SHIV-encephalitis. J Med Primatol. 2003;32;229-239.

(17) Gabuzda D H, Sobel R A. HIV antigen in brains of patients with AIDS. Ann Neurol. 1987;22:668.

(18) Buch S, Pinson D, King C L et al. Inhibitory and enhancing effects of IFN-gamma and IL-4 on SHIV(KU) replication in rhesus macaque macrophages: correlation between Th2 cytokines and productive infection in tissue macrophages during late-stage infection. Cytokine JID—9005353. 2001;13:295-304.

(19) Raghavan R, Stephens E B, Joag S V et al. Neuropathogenesis of chimeric simian/human immunodeficiency virus infection in pig-tailed and rhesus macaques. Brain Pathol. 1997;7:851-861.

(20) Smith M S, Niu Y, Li Z et al. Systemic Infection and Limited Replication of SHIV Vaccine Virus in Brains of Macaques Inoculated Intracerebrally with Infectious Viral DNA. Virology. Sep. 15, 2002;301(1):130-5.

(21) Hicks A, Potula R, Sui Y J et al. Neuropathogenesis of lentiviral infection in macaques: roles of CXCR4 and CCR5 viruses and interleukin-4 in enhancing monocyte chemoattractant protein-1 production in macrophages. Am J Pathol. 2002;161:813-822.

(22) Wang J, Harada A, Matsushita S et al. IL-4 and a glucocorticoid up-regulate CXCR4 expression on human CD4$^+$ T lymphocytes and enhance HIV-1 replication. J. Leukoc Biol. 1998;64:642-649.

(23) Jekle A., Keppler O. T., De Clercq E. et al. In vivo evolution of human immunodeficiency virus type 1 toward increased pathogenicity through CXCR4-mediated killing of uninfected CD4 T cells. J Virol. 2003;77:5846-5854.

(24) Pearce E. J., Caspar P., Grzych J. M., Lewis F A, Sher. A. Downregulation of Th1 cytokine production accompanies induction of Th2 responses by a parasitic helminth, *Schistosoma mansoni*. J Exp Med. 1991;173:159-166.

(25) Schramm G, Falcone F H, Gronow A et al. Molecular characterization of an interleukin-4-inducing factor from *Schistosoma mansoni* eggs. J Biol Chem. 2003;278:18384-18392.

(26) Dinesh K. Singh, Zhenqian Liu, Darlene Sheffer et al. A Non-infectious SHIV DNA Vaccine That Protects Macaques Against AIDS, J. Virol. 2005 March;79(6):3419-28.

(27) Weichold F F, Lisziewicz J, Zeman R A et al. Antisense phosphorothioate oligodeoxynucleotides alter HIV type 1 replication in cultured human macrophages and peripheral blood mononuclear cells. AIDS Res Hum Retroviruses. 1995; 11:863-867.

(28) Kim S G, Hatta T, Tsukahara S et al. Antiviral effect of phosphorothioate oligodeoxyribonucleotides complementary to human immunodeficiency virus. Bioorg Med Chem. 1995;3:49-54.

(29) Mautino M R, Morgan R A. Potent inhibition of human immunodeficiency virus type 1 replication by conditionally replicating human immunodeficiency virus based lentiviral vectors expressing envelope antisense mRNA. Hum Gene Ther. 2000; 11:2025-2037.

(30) Morris K V, Rossi J J. Anti-HIV-1 gene expressing lentiviral vectors as an adjunctive therapy for HIV-1 infection. Curr HIV Res. 2004;2:185-191.

(31) Brenner B G, Turner D, Wainberg M A. HIV-1 drug resistance: can we overcome? Expert Opin Biol Ther. 2002; 2:751-761.

(32) Dhillon N K, Sui Y, Potula R, Dhillon S, Adany I, Li Z, Villinger F, Pinson D, Naryan O, Buch S. Inhibition of pathogenic SHIV replication in macaques treated with antisense DNA of interleukin-4. Blood. Dec. 23, 2004 (electronically).

(33) Doranz, B. J., J. Rucker, Y. Yi, R. J. Smyth, M. Samson, S. C. Peiper, M. Parmentier, R. G. Collman, and R. W. Doms. 1996. A dual-tropic primary HIV-1 isolate that uses fusin and the beta-chemokine receptors CKR-5, CKR-3, and CKR-2b as fusion cofactors. *Cell* JID—0413066 85:1149-1158.

(34) Kumar, A., J. D. Lifson, Z. Li, F. Jia, S. Mukherjee, I. Adany, Z. Liu, M. Piatak, D. Sheffer, H. M. McClure, and O. Narayan. 2001. Sequential immunization of macaques with two differentially attenuated vaccines induced long-term virus-specific immune responses and conferred protection against AIDS caused by heterologous simian human immunodeficiency Virus (SHIV$_{(89.6)}$P). *Virology* JID—0110674 279:241-256.

(35) Singh, D. K., Z. Liu, D. Sheffer, G. A. Mackay, M. Smith, S. Dhillon, R. Hegde, F. Jia, I. Adany, and O. Narayan. 2005. A Noninfectious Simian/Human Immunodeficiency Virus DNA Vaccine That Protects Macaques against AIDS. *J Virol* 79:3419-3428.

(36) Villacres, M. C. and C. C. Bergmann. 1999. Enhanced cytotoxic T cell activity in IL-4-deficient mice. *J Immunol*. 162:2663-2670.

(37) Kienzle, N., K. Buttigieg, P. Groves, T. Kawula, and A. Kelso. 2002. A clonal culture system demonstrates that IL-4 induces a subpopulation of noncytolytic T cells with low CD8, perforin, and granzyme expression. *J Immunol*. 168: 1672-1681.

(38) Wang, J., K. Crawford, M. Yuan, H. Wang, P. R. Gorry, and D. Gabuzda. 2002. Regulation of CC chemokine receptor 5 and CD4 expression and human immunodeficiency virus type 1 replication in human macrophages and microglia by T helper type 2 cytokines. *J Infect. Dis*. 185:885-897.

From the foregoing it will be seen that this invention is one well adapted to attain all ends and objectives herein-above set forth, together with the other advantages which are obvious and which are inherent to the invention. Various modifications may of course be made, and the invention is not limited to the specific forms or arrangement of components and steps described herein, except insofar as such limitations are included in the following claims. Further, it will be understood that certain features and subcombinations are of utility and may be employed without reference to other features and subcombinations. This is contemplated by and is within the scope of the claims. In short, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

What is claimed and desired to be secured by Letters Patent is as follows:

1. A method of inhibiting SHIV or HIV viral replication in vitro or SHIV viral replication in a non-human subject comprising administering to an infected cell an antisense IL-4 nucleic acid and a DNA construct having a sequence encoding at least one viral protein capable of stimulating an immune response against HIV and having one or more non-functional genes that render the DNA construct non-pathogenic, and observing decreased SHIV or HIV viral replication.

2. The method of claim 1, wherein the nucleic acid is antisense DNA of IL-4.

3. The method of claim 1 wherein said host cell is a macrophage.

4. The method of claim 1 wherein said host cell is selected from a group of cells consisting of liver, spleen, and lymph node cells.

5. The method of claim 1 wherein said antisense IL4 nucleic acid is administered with a pharmaceutically acceptable carrier.

6. A method of treating or inhibiting SHIV replication in a non-human subject having or at risk of contracting a SHIV or infection comprising administering a therapeutically effective amount of an antisense IL-4 nucleic acid and a DNA construct having a sequence encoding at least one viral protein capable of stimulating an immune response against HIV and having one or more non-functional genes that render the DNA construct non-pathogenic.

7. The method of claim 6 wherein the nucleic acid is antisense DNA of IL-4.

8. The method of claim 6 wherein said antisense IL-4 nucleic acid is administered in a pharmaceutically acceptable carrier.

9. The method of claim 6 wherein the subject is selected from the group consisting of a macaque, and a mouse.

10. The method of claim 6 wherein administration is performed using a route selected from the group consisting of subcutaneous, intramuscular, intranasal, intraarterial, intravenous, topical, transvaginal, transdermal and transanal administration.

11. The method of claim 6 wherein the antisense IL-4 nucleic acid is encapsulated in a liposome.

12. The method of claim 6 wherein the subject is also administered at least one of the group consisting of an antiviral agent, antibacterial agent, antifungal agent, anti-protozoal agent, nucleoside analog reverse transcriptase inhibitor, non-nucleoside reverse transcriptase inhibitor, protease inhibitor, and fusion inhibitor.

13. The method of claim 8, wherein the pharmaceutically acceptable carrier is granulocyte macrophage colony-stimulating factor.

14. The method of claim 6 further comprising measuring a reduction in the amount of plasma SHIV mRNA in said subject after administering the antisense IL-4 nucleic acid.

15. The method of claim 6, wherein reduction in the amount of SHIV mRNA is measured in one or more cells from tissue selected from the group consisting of lymph nodes, liver, lung, and spleen of said subject.

16. The method of claim 6 wherein the DNA construct is derived from a SHIV or HIV virus passaged prior to rendering one or more genes selected from the group consisting of SHIV reverse transcriptase, HIV reverse transcriptase, SHIV integrase, HIV integrase, SHIV Vif, and HIV Vif non-functional.

17. The method of claim 1 wherein the DNA construct is derived from a SHIV or HIV virus passaged prior to rendering one or more genes selected from the group consisting of SIV reverse transcriptase, HIV reverse transcriptase, SIV integrase, HIV integrase, SIV Vif, and HIV Vif non-functional.

* * * * *

```
                         SEQUENCE LISTING

<160> NUMBER OF SEQ ID NOS: 8

<210> SEQ ID NO 1
<211> LENGTH: 23
<212> TYPE: DNA
<213> ORGANISM: Macaca mulatta

<400> SEQUENCE: 1
gggctgctgc tggcttttg ctt                                         23

<210> SEQ ID NO 2
<211> LENGTH: 23
<212> TYPE: DNA
<213> ORGANISM: Macaca mulatta

<400> SEQUENCE: 2
aagcaaaaag ccagcagcag ccc                                        23

<210> SEQ ID NO 3
<211> LENGTH: 23
<212> TYPE: DNA
<213> ORGANISM: Macaca mulatta
<220> FEATURE:
<221> NAME/KEY: misc_feature
<223> OTHER INFORMATION: Artifical Sequence, Scrambled IL-4

<400> SEQUENCE: 3
gggctgatgc ggccttttg ctt                                         23

<210> SEQ ID NO 4
<211> LENGTH: 20
<212> TYPE: DNA
<213> ORGANISM: Macaca mulatta

<400> SEQUENCE: 4
tttcacaggc acaagcagct                                            20

<210> SEQ ID NO 5
<211> LENGTH: 17
<212> TYPE: DNA
<213> ORGANISM: Macaca mulatta

<400> SEQUENCE: 5
gccaggcccc agaggtt                                               17

<210> SEQ ID NO 6
<211> LENGTH: 24
<212> TYPE: DNA
<213> ORGANISM: Macaca mulatta
<220> FEATURE:
<221> NAME/KEY: misc_feature
<223> OTHER INFORMATION: Artifical

<400> SEQUENCE: 6
ccgattcctg aaacggctcg acag                                       24
```

-continued

```
<210> SEQ ID NO 7
<211> LENGTH: 21
<212> TYPE: DNA
<213> ORGANISM: Mus musculus

<400> SEQUENCE: 7
ccatggatat gcgaagcacc t                                    21

<210> SEQ ID NO 8
<211> LENGTH: 24
<212> TYPE: DNA
<213> ORGANISM: Mus musculus

<400> SEQUENCE: 8
ggctagcact tgagagagat catc                                 24
```